(12) United States Patent
Orengo et al.

(10) Patent No.: US 11,578,127 B2
(45) Date of Patent: Feb. 14, 2023

(54) ANTI-FC EPSILON-R1 ALPHA (FCεR1α) ANTIBODIES, BISPECIFIC ANTIGEN-BINDING MOLECULES THAT BIND FCεR1α AND CD3, AND USES THEREOF

(71) Applicant: Regeneron Pharmaceuticals, Inc., Tarrytown, NY (US)

(72) Inventors: Jamie M. Orengo, Cortlandt Manor, NY (US); Andre Limnander, New York, NY (US); Jee H. Kim, Ardsley, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 499 days.

(21) Appl. No.: 16/547,910

(22) Filed: Aug. 22, 2019

(65) Prior Publication Data
US 2020/0062844 A1    Feb. 27, 2020

Related U.S. Application Data

(60) Provisional application No. 62/721,921, filed on Aug. 23, 2018.

(51) Int. Cl.
*C07K 16/28*    (2006.01)

(52) U.S. Cl.
CPC ........ *C07K 16/2809* (2013.01); *C07K 16/283* (2013.01)

(58) Field of Classification Search
CPC .............. C07K 16/2809; C07K 16/283; C07K 2317/31; A61K 2039/505
See application file for complete search history.

(56) References Cited

U.S. PATENT DOCUMENTS

| | | | |
|---|---|---|---|
| 2006/0073142 A1 | 4/2006 | Chan et al. | |
| 2016/0039934 A1 * | 2/2016 | Zhukovsky | C07K 16/2878 530/389.1 |

FOREIGN PATENT DOCUMENTS

| | | | | |
|---|---|---|---|---|
| WO | 2017/053856 A1 | 3/2017 | | |
| WO | WO-2017053856 A1 * | 3/2017 | .............. | A61P 35/00 |

OTHER PUBLICATIONS

Lloyd et al. Modelling the human immune response: performance of a 1011 human antibody repertoire against a broad panel of therapeutically relevant antigens. Protein Engineering, Design & Selection vol. 22 No. 3 pp. 159-168, 2009. (Year: 2009).*

Van Lier et al. Induction of T cell proliferation with anti-CD3 switch-variant monoclonal antibodies: effects of heavy chain isotype in monocyte-dependent systems. Eur. J. Immunol. 1987.17: 1.599-1604 (Year: 1987).*

Turner et al. Signalling through the high-af® nity IgE receptor FceRI. Nature |vol. 402 | Supp | Nov. 25, 1999 (Year: 1999).*

Hong et al. Antibody to FcεRIα Suppresses Immunoglobulin E Binding to High-Affinity Receptor I in Allergic Inflammation. Yonsei Med J Nov. 2016;57(6):1412-1419 (Year: 2016).*

Brinkmann et al. The making of bispecific antibodies. mAbs, 9:2, 182-212. Jan. 10, 2017. (Year: 2017).*

Panowski et al. Preclinical Evaluation of a Potent Anti-Bcma CD3 Bispecific Molecule for the Treatment of Multiple Myeloma. Blood (2016) 128 (22) : 383. (Year: 2016).*

Hong et al., Antibody to FceRIa Suppresses Immunoglobulin E Binding to High-Affinity Receptor I in Allergic Inflammation. Yonsei Med J. Nov. 2016;57(6):1412-9.

Jackman et al., Development of a two-part strategy to identify a therapeutic human bispecific antibody that inhibits IgE receptor signaling. J Biol Chem. Jul. 2, 2010;285(27):20850-9.

Riske et al., High affinity human IgE receptor (Fc epsilon RI). Analysis of functional domains of the alpha-subunit with monoclonal antibodies. J Biol Chem. Jun. 15, 1991;266(17):11245-51.

* cited by examiner

*Primary Examiner* — Amy E Juedes
*Assistant Examiner* — Brian Hartnett
(74) *Attorney, Agent, or Firm* — McCarter & English, LLP; Marcie B. Clarke

(57) ABSTRACT

The present invention provides novel full-length human antibodies that bind to human Fc epsilon-R1 alpha (monospecific antibodies). The present invention also provides novel bispecific antibodies (bsAbs) that bind to both Fc epsilon-R1 alpha and CD3 and activate T cells via the CD3 complex in the presence of Fc epsilon-R1 alpha-expressing cells. The bispecific antigen-binding molecules of the invention are useful for the treatment of diseases and disorders in which an upregulated or induced Fc epsilon-R1 alpha-targeted immune response is desired and/or therapeutically beneficial. For example, the bispecific antibodies of the invention are useful for the treatment of allergies, including anaphylaxis.

17 Claims, No Drawings
Specification includes a Sequence Listing.

SEQUENCE LISTING

<160> NUMBER OF SEQ ID NOS: 63

<210> SEQ ID NO 1
<211> LENGTH: 360
<212> TYPE: DNA
<213> ORGANISM: Artificial Sequence
<220> FEATURE:
<223> OTHER INFORMATION: synthetic

<400> SEQUENCE: 1

```
caggtgcagc tgcaggagtc gggcccagga ctggtgaagc cttcggagac cctgtccctc      60
acctgcactg tctctggtga ctccatcagt gattactatt ggatctggat ccggcagccc     120
ccaggaaagg gactggagtg gattggatat atctattaca gtgggagcac caactacaac     180
ccctccctca agagtcgagt caccatatca gtagccacgt ccaagaacca gttctccctg     240
aagttgaggt ctgtgaccgc cgcagacacg gccatgtatt actgtgcgag acgaaataac     300
tggaaccacg tccgtgcttt tgatatctgg ggccaaggga caatggtcac cgtctcttca     360
```

<210> SEQ ID NO 2
<211> LENGTH: 120
<212> TYPE: PRT
<213> ORGANISM: Artificial Sequence
<220> FEATURE:
<223> OTHER INFORMATION: synthetic

<400> SEQUENCE: 2

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Asp Tyr
            20                  25                  30

Tyr Trp Ile Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Ala Thr Ser Lys Asn Gln Phe Ser Leu
65                  70                  75                  80

Lys Leu Arg Ser Val Thr Ala Ala Asp Thr Ala Met Tyr Tyr Cys Ala
                85                  90                  95

Arg Arg Asn Asn Trp Asn His Val Arg Ala Phe Asp Ile Trp Gly Gln
            100                 105                 110

Gly Thr Met Val Thr Val Ser Ser
        115                 120
```

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3

```
ggtgactcca tcagtgatta ctat                                              24
```

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Asp Ser Ile Ser Asp Tyr Tyr
1               5

<210> SEQ ID NO 5
<211> LENGTH: 21
<212> TYPE: DNA
<213> ORGANISM: Artificial Sequence
<220> FEATURE:
<223> OTHER INFORMATION: synthetic

<400> SEQUENCE: 5
atctattaca gtgggagcac c                                           21

<210> SEQ ID NO 6
<211> LENGTH: 7
<212> TYPE: PRT
<213> ORGANISM: Artificial Sequence
<220> FEATURE:
<223> OTHER INFORMATION: synthetic

<400> SEQUENCE: 6

Ile Tyr Tyr Ser Gly Ser Thr
1               5

<210> SEQ ID NO 7
<211> LENGTH: 42
<212> TYPE: DNA
<213> ORGANISM: Artificial Sequence
<220> FEATURE:
<223> OTHER INFORMATION: synthetic

<400> SEQUENCE: 7
gcgagacgaa ataactggaa ccacgtccgt gcttttgata tc                    42

<210> SEQ ID NO 8
<211> LENGTH: 14
<212> TYPE: PRT
<213> ORGANISM: Artificial Sequence
<220> FEATURE:
<223> OTHER INFORMATION: synthetic

<400> SEQUENCE: 8

Ala Arg Arg Asn Asn Trp Asn His Val Arg Ala Phe Asp Ile
1               5                   10

<210> SEQ ID NO 9
<211> LENGTH: 360
<212> TYPE: DNA
<213> ORGANISM: Artificial Sequence
<220> FEATURE:
<223> OTHER INFORMATION: synthetic

<400> SEQUENCE: 9
caggtgcagc tgcaggagtc gggcccagga ctggtgaagc cttcggagac cctgtccctc    60
acctgcactg tctctggtga ctccatcaat gattactact ggagctggct ccggcagccc   120
ccagggaagg gactggagtg gattgggtat atctattaca gtgggagcac caactacaac   180
ccctccctca agagtcgagt caccatatca gtagacacgt ccaagaacca gttctccctg   240
aagctgagct ctgtgaccgc cgctgacacg gccgtgtatt actgtacgag acgaaataac    300
tggaactacg tccgtgcttt tgatatctgg ggccaaggga caatggtcac cgtctcttca    360

<210> SEQ ID NO 10
<211> LENGTH: 120
<212> TYPE: PRT
<213> ORGANISM: Artificial Sequence
<220> FEATURE:
<223> OTHER INFORMATION: synthetic

<400> SEQUENCE: 10

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Asn Asp Tyr
            20                  25                  30

Tyr Trp Ser Trp Leu Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Thr
                85                  90                  95

Arg Arg Asn Asn Trp Asn Tyr Val Arg Ala Phe Asp Ile Trp Gly Gln
            100                 105                 110

Gly Thr Met Val Thr Val Ser Ser
        115                 120

<210> SEQ ID NO 11
<211> LENGTH: 24
<212> TYPE: DNA
<213> ORGANISM: Artificial Sequence
<220> FEATURE:
<223> OTHER INFORMATION: synthetic

<400> SEQUENCE: 11
ggtgactcca tcaatgatta ctac                                            24

<210> SEQ ID NO 12
<211> LENGTH: 8
<212> TYPE: PRT
<213> ORGANISM: Artificial Sequence
<220> FEATURE:
<223> OTHER INFORMATION: synthetic

<400> SEQUENCE: 12

Gly Asp Ser Ile Asn Asp Tyr Tyr
1               5

<210> SEQ ID NO 13
<211> LENGTH: 21
<212> TYPE: DNA
<213> ORGANISM: Artificial Sequence
<220> FEATURE:
<223> OTHER INFORMATION: synthetic

<400> SEQUENCE: 13
atctattaca gtgggagcac c                                               21

<210> SEQ ID NO 14
<211> LENGTH: 7

<212> TYPE: PRT
<213> ORGANISM: Artificial Sequence
<220> FEATURE:
<223> OTHER INFORMATION: synthetic

<400> SEQUENCE: 14

Ile Tyr Tyr Ser Gly Ser Thr
1               5

<210> SEQ ID NO 15
<211> LENGTH: 42
<212> TYPE: DNA
<213> ORGANISM: Artificial Sequence
<220> FEATURE:
<223> OTHER INFORMATION: synthetic

<400> SEQUENCE: 15
acgagacgaa ataactggaa ctacgtccgt gcttttgata tc                           42

<210> SEQ ID NO 16
<211> LENGTH: 14
<212> TYPE: PRT
<213> ORGANISM: Artificial Sequence
<220> FEATURE:
<223> OTHER INFORMATION: synthetic

<400> SEQUENCE: 16

Thr Arg Arg Asn Asn Trp Asn Tyr Val Arg Ala Phe Asp Ile
1               5                   10

<210> SEQ ID NO 17
<211> LENGTH: 360
<212> TYPE: DNA
<213> ORGANISM: Artificial Sequence
<220> FEATURE:
<223> OTHER INFORMATION: synthetic

<400> SEQUENCE: 17
caggtgcagg tgcaggagtc gggcccaaga ctggtgaagc cttcggagac cctgtccctc        60
acctgcactg tctctggtgg ctccatgagt agttactatt ggatttggat ccggcagccc       120
ccagggaagg aattggagtg gattgggtat atctattaca gtgggagcac caactacaac       180
ccctccctca gagtcgagc caccatatca gtagacacgt ccaagaatca gttctccctg       240
aacctgaact ctgtgaccgc cgcagacacg gccgtgtatt actgtgcgag acgaaataac       300
tggaactacg tccgtgcttt tgatatctgg ggccaaggga caatggtcac cgtctcttca       360

<210> SEQ ID NO 18
<211> LENGTH: 120
<212> TYPE: PRT
<213> ORGANISM: Artificial Sequence
<220> FEATURE:
<223> OTHER INFORMATION: synthetic

<400> SEQUENCE: 18

Gln Val Gln Val Gln Glu Ser Gly Pro Arg Leu Val Lys Pro Ser Glu
1               5                   10                  15

Thr Leu Ser Leu Thr Cys Thr Val Ser Gly Gly Ser Met Ser Ser Tyr
            20                  25                  30

Tyr Trp Ile Trp Ile Arg Gln Pro Pro Gly Lys Glu Leu Glu Trp Ile
        35                  40                  45

Gly Tyr Ile Tyr Tyr Ser Gly Ser Thr Asn Tyr Asn Pro Ser Leu Lys
    50                  55                  60

-continued

Ser Arg Ala Thr Ile Ser Val Asp Thr Ser Lys Asn Gln Phe Ser Leu
 65                  70                  75                  80

Asn Leu Asn Ser Val Thr Ala Ala Asp Thr Ala Val Tyr Tyr Cys Ala
                 85                  90                  95

Arg Arg Asn Asn Trp Asn Tyr Val Arg Ala Phe Asp Ile Trp Gly Gln
            100                 105                 110

Gly Thr Met Val Thr Val Ser Ser
            115                 120

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggtggctcca tgagtagtta ctat                                        24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

Gly Gly Ser Met Ser Ser Tyr Tyr
1               5

<210> SEQ ID NO 21
<211> LENGTH: 21
<212> TYPE: DNA
<213> ORGANISM: Artificial Sequence
<220> FEATURE:
<223> OTHER INFORMATION: synthetic

<400> SEQUENCE: 21
atctattaca gtgggagcac c                                           21

<210> SEQ ID NO 22
<211> LENGTH: 7
<212> TYPE: PRT
<213> ORGANISM: Artificial Sequence
<220> FEATURE:
<223> OTHER INFORMATION: synthetic

<400> SEQUENCE: 22

Ile Tyr Tyr Ser Gly Ser Thr
1               5

<210> SEQ ID NO 23
<211> LENGTH: 42
<212> TYPE: DNA
<213> ORGANISM: Artificial Sequence
<220> FEATURE:
<223> OTHER INFORMATION: synthetic

<400> SEQUENCE: 23
gcgagacgaa ataactggaa ctacgtccgt gcttttgata tc                    42

<210> SEQ ID NO 24
<211> LENGTH: 14
<212> TYPE: PRT
<213> ORGANISM: Artificial Sequence
<220> FEATURE:
<223> OTHER INFORMATION: synthetic

<400> SEQUENCE: 24

Ala Arg Arg Asn Asn Trp Asn Tyr Val Arg Ala Phe Asp Ile
1               5                   10

<210> SEQ ID NO 25
<211> LENGTH: 324
<212> TYPE: DNA
<213> ORGANISM: Artificial Sequence
<220> FEATURE:
<223> OTHER INFORMATION: synthetic

<400> SEQUENCE: 25
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccgtca     180
aggttcagtg gcagtggatc tgggacagat ttcactctca ccatcagcag tctgcaacct     240
gaagattttg caacttacta ctgtcaacag agttacagta cccctccgat caccttcggc     300
caagggacac gactggagat taaa                                            324

<210> SEQ ID NO 26
<211> LENGTH: 108
<212> TYPE: PRT
<213> ORGANISM: Artificial Sequence
<220> FEATURE:
<223> OTHER INFORMATION: synthetic

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27
cagagcatta gcagctat                                                    18

<210> SEQ ID NO 28
<211> LENGTH: 6
<212> TYPE: PRT
<213> ORGANISM: Artificial Sequence
<220> FEATURE:

```
<223> OTHER INFORMATION: synthetic

<400> SEQUENCE: 28

Gln Ser Ile Ser Ser Tyr
1               5

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 gctgcatcc                                                                  9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Ala Ala Ser
1

<210> SEQ ID NO 31
<211> LENGTH: 30
<212> TYPE: DNA
<213> ORGANISM: Artificial Sequence
<220> FEATURE:
<223> OTHER INFORMATION: synthetic

<400> SEQUENCE: 31
caacagagtt acagtacccc tccgatcacc                                          30

<210> SEQ ID NO 32
<211> LENGTH: 10
<212> TYPE: PRT
<213> ORGANISM: Artificial Sequence
<220> FEATURE:
<223> OTHER INFORMATION: synthetic

<400> SEQUENCE: 32

Gln Gln Ser Tyr Ser Thr Pro Pro Ile Thr
1               5                   10

<210> SEQ ID NO 33
<211> LENGTH: 1344
<212> TYPE: DNA
<213> ORGANISM: Artificial Sequence
<220> FEATURE:
<223> OTHER INFORMATION: synthetic

<400> SEQUENCE: 33
caggtgcagc tgcaggagtc gggcccagga ctggtgaagc cttcggagac cctgtccctc        60
acctgcactg tctctggtga ctccatcagt gattactatt ggatctggat ccggcagccc       120
ccaggaaagg gactggagtg gattggatat atctattaca gtgggagcac caactacaac       180
ccctccctca gagtcgagt caccatatca gtagccacgt ccaagaacca gttctccctg        240
aagttgaggt ctgtgaccgc cgcagacacg gccatgtatt actgtgcgag acgaaataac       300
tggaaccacg tccgtgcttt tgatatctgg ggccaaggga caatggtcac cgtctcttca      360
```

```
gcctccacca agggcccatc ggtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacctgca acgtagatca caagcccagc aacaccaagg tggacaagag agttgagtcc    660
aaatatggtc ccccatgccc accctgccca gcacctgagt tcctgggggg accatcagtc    720
ttcctgttcc ccccaaaacc caaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtct ccaacaaagg cctcccgtcc tccatcgaga aaaccatctc caaagccaaa   1020
gggcagcccc gagagccaca ggtgtacacc ctgcccccat cccaggagga tgaccaag     1080 aaccaggtca gcctgacctg cctggtcaaa ggcttctacc ccagcgacat cgccgtggag   1140
tgggagagca atgggcagcc ggagaacaac tacaagacca cgcctcccgt gctggactcc   1200
gacggctcct tcttcctcta cagcaggctc accgtggaca agagcaggtg gcaggagggg   1260
aatgtcttct catgctccgt gatgcatgag gctctgcaca accactacac acagaagtcc   1320 ctctcccctgt ctctgggtaa atga                                         1344
```

<210> SEQ ID NO 34
<211> LENGTH: 447
<212> TYPE: PRT
<213> ORGANISM: Artificial Sequence
<220> FEATURE:
<223> OTHER INFORMATION: synthetic

<400> SEQUENCE: 34

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Asp Tyr
            20                  25                  30

Tyr Trp Ile Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Ala Thr Ser Lys Asn Gln Phe Ser Leu
65                  70                  75                  80

Lys Leu Arg Ser Val Thr Ala Ala Asp Thr Ala Met Tyr Tyr Cys Ala
                85                  90                  95

Arg Arg Asn Asn Trp Asn His Val Arg Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly Lys
        435                 440                 445

<210> SEQ ID NO 35
<211> LENGTH: 1344
<212> TYPE: DNA
<213> ORGANISM: Artificial Sequence
<220> FEATURE:
<223> OTHER INFORMATION: synthetic

<400> SEQUENCE: 35
caggtgcagc tgcaggagtc gggcccagga ctggtgaagc cttcggagac cctgtccctc      60
acctgcactg tctctggtga ctccatcaat gattactact ggagctggct ccggcagccc     120
ccagggaagg gactggagtg gattgggtat atctattaca gtgggagcac caactacaac     180
ccctccctca gagtcgagt caccatatca gtagacacgt ccaagaacca gttctccctg     240
aagctgagct ctgtgaccgc cgctgacacg gccgtgtatt actgtacgag acgaaataac     300
tggaactacg tccgtgcttt tgatatctgg ggccaaggga caatggtcac cgtctcttca     360
gcctccacca agggcccatc ggtcttcccc ctggcgccct gctccaggag cacctccgag     420
agcacagccg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacgaagacc     600
```

```
tacacctgca acgtagatca caagcccagc aacaccaagg tggacaagag agttgagtcc    660
aaatatggtc ccccatgccc accctgccca gcacctgagt tcctgggggg accatcagtc    720
ttcctgttcc ccccaaaacc caaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtct ccaacaaagg cctcccgtcc tccatcgaga aaaccatctc caaagccaaa   1020
gggcagcccc gagagccaca ggtgtacacc ctgcccccat cccaggagga tgaccaag     1080 aaccaggtca gcctgacctg cctggtcaaa ggcttctacc ccagcgacat cgccgtggag   1140
tgggagagca atgggcagcc ggagaacaac tacaagacca cgcctcccgt gctggactcc   1200
gacggctcct tcttcctcta cagcaggctc accgtggaca agagcaggtg gcaggagggg   1260
aatgtcttct catgctccgt gatgcatgag gctctgcaca accactacac acagaagtcc   1320 ctctcccctgt ctctgggtaa atga                                          1344
```

<210> SEQ ID NO 36
<211> LENGTH: 447
<212> TYPE: PRT
<213> ORGANISM: Artificial Sequence
<220> FEATURE:
<223> OTHER INFORMATION: synthetic

<400> SEQUENCE: 36

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Asn Asp Tyr
            20                  25                  30

Tyr Trp Ser Trp Leu Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Thr
                85                  90                  95

Arg Arg Asn Asn Trp Asn Tyr Val Arg Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
```

```
            225                 230                 235                 240
Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
        435                 440                 445

<210> SEQ ID NO 37
<211> LENGTH: 1344
<212> TYPE: DNA
<213> ORGANISM: Artificial Sequence
<220> FEATURE:
<223> OTHER INFORMATION: synthetic

<400> SEQUENCE: 37
caggtgcagg tgcaggagtc gggcccaaga ctggtgaagc cttcggagac cctgtccctc        60
acctgcactg tctctggtgg ctccatgagt agttactatt ggatttggat ccggcagccc       120
ccagggaagg aattggagtg gattgggtat atctattaca gtgggagcac caactacaac       180
ccctccctca gagtcgagc accatatca gtagacacgt ccaagaatca gttctccctg         240
aacctgaact ctgtgaccgc cgcagacacg gccgtgtatt actgtgcgag acgaaataac       300
tggaactacg tccgtgcttt tgatatctgg ggccaaggga caatggtcac cgtctcttca      360
gcctccacca agggcccatc ggtcttcccc ctggcgccct gctccaggag cacctccgag      420
agcacagccg ccctgggctg cctggtcaag gactacttcc ccgaaccggt gacggtgtcg      480
tggaactcag gcgccctgac cagcggcgtg cacaccttcc cggctgtcct acagtcctca      540
ggactctact ccctcagcag cgtggtgacc gtgccctcca gcagcttggg cacgaagacc      600
tacacctgca acgtagatca caagcccagc aacaccaagg tggacaagag agttgagtcc      660
aaatatggtc cccatgccca ccctgccca gcacctgagt tcctggggg accatcagtc        720 ttcctgttcc cccaaaaccc aaggacact ctcatgatct cccggacccc tgaggtcacg        780
tgcgtggtgg tggacgtgag ccaggaagac cccgaggtcc agttcaactg gtacgtggat      840
```

```
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtct ccaacaaagg cctcccgtcc tccatcgaga aaaccatctc caaagccaaa   1020
gggcagcccc gagagccaca ggtgtacacc ctgcccccat cccaggagga tgaccaag     1080
aaccaggtca gcctgacctg cctggtcaaa ggcttctacc ccagcgacat cgccgtggag   1140
tgggagagca atgggcagcc ggagaacaac tacaagacca cgcctcccgt gctggactcc   1200
gacggctcct tcttcctcta cagcaggctc accgtggaca agagcaggtg gcaggagggg   1260
aatgtcttct catgctccgt gatgcatgag gctctgcaca accactacac acagaagtcc   1320
ctctccctgt ctctgggtaa atga                                          1344
```

<210> SEQ ID NO 38
<211> LENGTH: 447
<212> TYPE: PRT
<213> ORGANISM: Artificial Sequence
<220> FEATURE:
<223> OTHER INFORMATION: synthetic

<400> SEQUENCE: 38

```
Gln Val Gln Val Gln Glu Ser Gly Pro Arg Leu Val Lys Pro Ser Glu
1               5                   10                  15

Thr Leu Ser Leu Thr Cys Thr Val Ser Gly Gly Ser Met Ser Ser Tyr
            20                  25                  30

Tyr Trp Ile Trp Ile Arg Gln Pro Pro Gly Lys Glu Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Asn Leu Asn Ser Val Thr Ala Ala Asp Thr Ala Val Tyr Tyr Cys Ala
                85                  90                  95

Arg Arg Asn Asn Trp Asn Tyr Val Arg Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270
```

Val Gln Phe Asn Trp Tyr Val Asp Gly Val Glu Val His Asn Ala Lys
              275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 39
<211> LENGTH: 645
<212> TYPE: DNA
<213> ORGANISM: Artificial Sequence
<220> FEATURE:
<223> OTHER INFORMATION: synthetic

<400> SEQUENCE: 39
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccgtca    180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645

<210> SEQ ID NO 40
<211> LENGTH: 214
<212> TYPE: PRT
<213> ORGANISM: Artificial Sequence
<220> FEATURE:
<223> OTHER INFORMATION: synthetic

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr

```
                20                  25                  30
Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Ile Thr Phe Gly Gln Gly Thr Arg Leu Glu Ile Lys Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 41
<211> LENGTH: 372
<212> TYPE: DNA
<213> ORGANISM: Artificial Sequence
<220> FEATURE:
<223> OTHER INFORMATION: synthetic

<400> SEQUENCE: 41
gaagtacagc ttgtagaatc cggcggagga ctggtacaac ctggaagaag tcttagactg    60
agttgcgcag ctagtgggtt tacattcgac gattacagca tgcattgggt gaggcaagct   120
cctggtaaag gattgaatg ggttagcggg atatcatgga actcaggaag catcggatac    180
gccgacagcg tgaaaggccg atttacaata tctagggaca cgcaaaaaa ctctctctac    240 cttcaaatga actctcttag gcagaagac acagcattgt attattgcgc aaaatacggc    300
agtggttatg gcaagtttta ttattatgga atggacgtgt ggggacaagg gacaacagtg   360
acagtgagta gc                                                       372

<210> SEQ ID NO 42
<211> LENGTH: 124
<212> TYPE: PRT
<213> ORGANISM: Artificial Sequence
<220> FEATURE:
<223> OTHER INFORMATION: synthetic

<400> SEQUENCE: 42

Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
             20                  25                  30

Ser Met His Trp Val Arg Gln Ala Pro Gly Lys Gly Leu Glu Trp Val
```

35                  40                  45
Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr Tyr Tyr Gly Met Asp
            100                 105                 110

Val Trp Gly Gln Gly Thr Thr Val Thr Val Ser Ser
        115                 120

<210> SEQ ID NO 43
<211> LENGTH: 24
<212> TYPE: DNA
<213> ORGANISM: Artificial Sequence
<220> FEATURE:
<223> OTHER INFORMATION: synthetic

<400> SEQUENCE: 43
gggtttacat tcgacgatta cagc                                          24

<210> SEQ ID NO 44
<211> LENGTH: 8
<212> TYPE: PRT
<213> ORGANISM: Artificial Sequence
<220> FEATURE:
<223> OTHER INFORMATION: synthetic

<400> SEQUENCE: 44

Gly Phe Thr Phe Asp Asp Tyr Ser
1               5

<210> SEQ ID NO 45
<211> LENGTH: 24
<212> TYPE: DNA
<213> ORGANISM: Artificial Sequence
<220> FEATURE:
<223> OTHER INFORMATION: synthetic

<400> SEQUENCE: 45
atatcatgga actcaggaag catc                                          24

<210> SEQ ID NO 46
<211> LENGTH: 8
<212> TYPE: PRT
<213> ORGANISM: Artificial Sequence
<220> FEATURE:
<223> OTHER INFORMATION: synthetic

<400> SEQUENCE: 46

Ile Ser Trp Asn Ser Gly Ser Ile
1               5

<210> SEQ ID NO 47
<211> LENGTH: 51
<212> TYPE: DNA
<213> ORGANISM: Artificial Sequence
<220> FEATURE:
<223> OTHER INFORMATION: synthetic

<400> SEQUENCE: 47
gcaaaatacg gcagtggtta tggcaagttt tattattatg gaatggacgt g            51

<210> SEQ ID NO 48
<211> LENGTH: 17
<212> TYPE: PRT
<213> ORGANISM: Artificial Sequence
<220> FEATURE:
<223> OTHER INFORMATION: synthetic

<400> SEQUENCE: 48

Ala Lys Tyr Gly Ser Gly Tyr Gly Lys Phe Tyr Tyr Tyr Gly Met Asp
1               5                   10                  15

Val

<210> SEQ ID NO 49
<211> LENGTH: 1341
<212> TYPE: DNA
<213> ORGANISM: Artificial Sequence
<220> FEATURE:
<223> OTHER INFORMATION: synthetic

<400> SEQUENCE: 49
caggtgcagc tgcaggagtc gggcccagga ctggtgaagc cttcggagac cctgtccctc      60
acctgcactg tctctggtga ctccatcagt gattactatt ggatctggat ccggcagccc     120
ccaggaaagg gactggagtg gattggatat atctattaca gtgggagcac caactacaac     180
ccctccctca gagtcgagt caccatatca gtagccacgt ccaagaacca gttctccctg      240
aagttgaggt ctgtgaccgc cgcagacacg gccatgtatt actgtgcgag acgaaataac     300
tggaaccacg tccgtgcttt tgatatctgg ggccaaggga caatggtcac cgtctcttca     360
gcctccacca agggcccatc ggtcttcccc ctggcgccct gctccaggag cacctccgag     420
agcacagccg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacgaagacc     600
tacacctgca acgtagatca caagcccagc aacaccaagg tggacaagag agttgagtcc     660
aaatatggtc cccatgccc accgtgccca gcaccacctg tggcaggacc atcagtcttc     720
ctgttccccc caaaacccaa ggacactctc atgatctccc ggacccctga ggtcacgtgc     780
gtggtggtgg acgtgagcca ggaagacccc gaggtccagt tcaactggta cgtggatggc     840
gtggaggtgc ataatgccaa gacaaagccg cgggaggagc agttcaacag cacgtaccgt     900
gtggtcagcg tcctcaccgt cctgcaccag gactggctga acggcaagga gtacaagtgc     960
aaggtctcca acaaaggcct cccgtcctcc atcgagaaaa ccatctccaa agccaaaggg    1020
cagccccgag agccacaggt gtacaccctg cccccatccc aggaggagat gaccaagaac    1080
caggtcagcc tgacctgcct ggtcaaaggc ttctacccca gcgacatcgc cgtggagtgg    1140
gagagcaatg ggcagccgga gaacaactac aagaccacgc ctcccgtgct ggactccgac    1200
ggctccttct tcctctacag caggctcacc gtggacaaga gcaggtggca ggaggggaat    1260
gtcttctcat gctccgtgat gcatgaggct ctgcacaacc actacacaca gaagtccctc    1320
tccctgtctc tgggtaaatg a                                              1341

<210> SEQ ID NO 50
<211> LENGTH: 446
<212> TYPE: PRT
<213> ORGANISM: Artificial Sequence
<220> FEATURE:
<223> OTHER INFORMATION: synthetic

```
<400> SEQUENCE: 50

Gln Val Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Ser Asp Tyr
            20                  25                  30

Tyr Trp Ile Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
 50                  55                  60

Ser Arg Val Thr Ile Ser Val Ala Thr Ser Lys Asn Gln Phe Ser Leu
 65                  70                  75                  80

Lys Leu Arg Ser Val Thr Ala Ala Asp Thr Ala Met Tyr Tyr Cys Ala
            85                  90                  95

Arg Arg Asn Asn Trp Asn His Val Arg Ala Phe Asp Ile Trp Gly Gln
        100                 105                 110

Gly Thr Met Val Thr Val Ser Ser Ala Ser Thr Lys Gly Pro Ser Val
    115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415
```

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
            435                 440                 445

<210> SEQ ID NO 51
<211> LENGTH: 1341
<212> TYPE: DNA
<213> ORGANISM: Artificial Sequence
<220> FEATURE:
<223> OTHER INFORMATION: synthetic

<400> SEQUENCE: 51

| | |
|---|---|
| caggtgcagc tgcaggagtc gggcccagga ctggtgaagc cttcggagac cctgtccctc | 60 |
| acctgcactg tctctggtga ctccatcaat gattactact ggagctggct ccggcagccc | 120 |
| ccagggaagg gactggagtg gattgggtat atctattaca gtgggagcac caactacaac | 180 |
| ccctccctca gagtcgagt caccatatca gtagacacgt ccaagaacca gttctccctg | 240 |
| aagctgagct ctgtgaccgc cgctgacacg gccgtgtatt actgtacgag acgaaataac | 300 |
| tggaactacg tccgtgctttt tgatatctgg ggccaaggga caatggtcac cgtctcttca | 360 |
| gcctccacca agggcccatc ggtcttcccc ctggcgccct gctccaggag cacctccgag | 420 |
| agcacagccg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgccctcca gcagcttggg cacgaagacc | 600 |
| tacacctgca acgtagatca caagcccagc aacaccaagg tggacaagag agttgagtcc | 660 |
| aaatatggtc ccccatgccc accgtgccca gcaccacctg tggcaggacc atcagtcttc | 720 |
| ctgttccccc caaaacccaa ggacactctc atgatctccc ggacccctga ggtcacgtgc | 780 |
| gtggtggtgg acgtgagcca ggaagacccc gaggtccagt tcaactggta cgtggatggc | 840 |
| gtggaggtgc ataatgccaa gacaaagccg cgggaggagc agttcaacag cacgtaccgt | 900 |
| gtggtcagcg tcctcaccgt cctgcaccag gactggctga acggcaagga gtacaagtgc | 960 |
| aaggtctcca acaaaggcct cccgtcctcc atcgagaaaa ccatctccaa agccaaaggg | 1020 |
| cagccccgag agccacaggt gtacaccctg cccccatccc aggaggagat gaccaagaac | 1080 |
| caggtcagcc tgacctgcct ggtcaaaggc ttctacccca gcgacatcgc cgtggagtgg | 1140 |
| gagagcaatg ggcagccgga gaacaactac aagaccacgc ctcccgtgct ggactccgac | 1200 |
| ggctccttct tcctctacag caggctcacc gtggacaaga gcaggtggca ggaggggaat | 1260 |
| gtcttctcat gctccgtgat gcatgaggct ctgcacaacc actacacaca gaagtccctc | 1320 |
| tccctgtctc tgggtaaatg a | 1341 |

<210> SEQ ID NO 52
<211> LENGTH: 446
<212> TYPE: PRT
<213> ORGANISM: Artificial Sequence
<220> FEATURE:
<223> OTHER INFORMATION: synthetic

<400> SEQUENCE: 52

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Asn Asp Tyr
            20                  25                  30

-continued

```
Tyr Trp Ser Trp Leu Arg Gln Pro Gly Lys Gly Leu Glu Trp Ile
         35                  40                  45
Gly Tyr Ile Tyr Tyr Ser Gly Ser Thr Asn Tyr Asn Pro Ser Leu Lys
 50                  55                  60
Ser Arg Val Thr Ile Ser Val Asp Thr Ser Lys Asn Gln Phe Ser Leu
 65                  70                  75                  80
Lys Leu Ser Ser Val Thr Ala Ala Asp Thr Ala Val Tyr Tyr Cys Thr
                 85                  90                  95
Arg Arg Asn Asn Trp Asn Tyr Val Arg Ala Phe Asp Ile Trp Gly Gln
                 100                 105                 110
Gly Thr Met Val Thr Val Ser Ser Ala Ser Thr Lys Gly Pro Ser Val
             115                 120                 125
Phe Pro Leu Ala Pro Cys Ser Arg Ser Thr Ser Glu Ser Thr Ala Ala
         130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                 165                 170                 175
Leu Gln Ser Ser Gly Leu Tyr Ser Leu Ser Ser Val Val Thr Val Pro
             180                 185                 190
Ser Ser Ser Leu Gly Thr Lys Thr Tyr Thr Cys Asn Val Asp His Lys
         195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Pro Val Ala Gly Pro Ser Val Phe
225                 230                 235                 240
Leu Phe Pro Pro Lys Pro Lys Asp Thr Leu Met Ile Ser Arg Thr Pro
                 245                 250                 255
Glu Val Thr Cys Val Val Val Asp Val Ser Gln Glu Asp Pro Glu Val
             260                 265                 270
Gln Phe Asn Trp Tyr Val Asp Gly Val Glu Val His Asn Ala Lys Thr
         275                 280                 285
Lys Pro Arg Glu Glu Gln Phe Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                 325                 330                 335
Lys Ala Lys Gly Gln Pro Arg Glu Pro Gln Val Tyr Thr Leu Pro Pro
             340                 345                 350
Ser Gln Glu Glu Met Thr Lys Asn Gln Val Ser Leu Thr Cys Leu Val
         355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                 405                 410                 415
Gln Glu Gly Asn Val Phe Ser Cys Ser Val Met His Glu Ala Leu His
             420                 425                 430
Asn His Tyr Thr Gln Lys Ser Leu Ser Leu Ser Leu Gly Lys
         435                 440                 445
```

<210> SEQ ID NO 53
<211> LENGTH: 1341
<212> TYPE: DNA
<213> ORGANISM: Artificial Sequence
<220> FEATURE:
<223> OTHER INFORMATION: synthetic

<400> SEQUENCE: 53

```
caggtgcagg tgcaggagtc gggcccaaga ctggtgaagc cttcggagac cctgtccctc      60
acctgcactg tctctggtgg ctccatgagt agttactatt ggatttggat ccggcagccc     120
ccagggaagg aattggagtg gattgggtat atctattaca gtgggagcac caactacaac     180
ccctccctca gagtcgagc accatatca gtagacacgt ccaagaatca gttctccctg      240
aacctgaact ctgtgaccgc cgcagacacg gccgtgtatt actgtgcgag acgaaataac     300
tggaactacg tccgtgcttt tgatatctgg ggccaaggga caatggtcac cgtctcttca     360
gcctccacca agggcccatc ggtcttcccc ctggcgccct gctccaggag cacctccgag     420
agcacagccg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacgaagacc     600
tacacctgca acgtagatca caagcccagc aacaccaagg tggacaagag agttgagtcc     660
aaatatggtc ccccatgccc accgtgccca gcaccacctg tggcaggacc atcagtcttc     720
ctgttccccc caaaacccaa ggacactctc atgatctccc ggacccctga ggtcacgtgc     780
gtggtggtgg acgtgagcca ggaagacccc gaggtccagt tcaactggta cgtggatggc     840
gtggaggtgc ataatgccaa gacaaagccg cgggaggagc agttcaacag cacgtaccgt     900
gtggtcagcg tcctcaccgt cctgcaccag gactggctga acggcaagga gtacaagtgc     960
aaggtctcca acaaaggcct cccgtcctcc atcgagaaaa ccatctccaa agccaaaggg    1020
cagccccgag agccacaggt gtacaccctg cccccatccc aggaggagat gaccaagaac    1080
caggtcagcc tgacctgcct ggtcaaaggc ttctacccca gcgacatcgc cgtggagtgg    1140
gagagcaatg ggcagccgga gaacaactac aagaccacgc ctcccgtgct ggactccgac    1200
ggctccttct tcctctacag caggctcacc gtggacaaga gcaggtggca ggaggggaat    1260
gtcttctcat gctccgtgat gcatgaggct ctgcacaacc actacacaca gaagtccctc    1320
tccctgtctc tgggtaaatg a                                              1341
```

<210> SEQ ID NO 54
<211> LENGTH: 446
<212> TYPE: PRT
<213> ORGANISM: Artificial Sequence
<220> FEATURE:
<223> OTHER INFORMATION: synthetic

<400> SEQUENCE: 54

```
Gln Val Gln Val Gln Glu Ser Gly Pro Arg Leu Val Lys Pro Ser Glu
1               5                   10                  15

Thr Leu Ser Leu Thr Cys Thr Val Ser Gly Gly Ser Met Ser Ser Tyr
            20                  25                  30

Tyr Trp Ile Trp Ile Arg Gln Pro Pro Gly Lys Glu Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80
```

Asn Leu Asn Ser Val Thr Ala Ala Asp Thr Ala Val Tyr Tyr Cys Ala
                85                  90                  95

Arg Arg Asn Asn Trp Asn Tyr Val Arg Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 55
<211> LENGTH: 1353
<212> TYPE: DNA
<213> ORGANISM: Artificial Sequence
<220> FEATURE:
<223> OTHER INFORMATION: synthetic

<400> SEQUENCE: 55

```
gaagtacagc ttgtagaatc cggcggagga ctggtacaac ctggaagaag tcttagactg    60
agttgcgcag ctagtgggtt tacattcgac gattacagca tgcattgggt gaggcaagct   120
cctggtaaag gattgaatg ggttagcggg atatcatgga actcaggaag catcggatac    180
gccgacagcg tgaaaggccg atttacaata tctaggaca acgcaaaaaa ctctctctac    240
cttcaaatga actctcttag ggcagaagac acagcattgt attattgcgc aaaatacggc   300
agtggttatg gcaagtttta ttattatgga atggacgtgt ggggacaagg acaacagtg    360 acagtgagta gcgccagcac aaaaggtcct agcgttttc cacttgcccc atgttcaagg    420
tcaacctccg aaagtaccgc cgctcttggc tgtctcgtaa agattatttt tcccgaacct   480
gtaactgtct cctggaactc cggcgcactc acttccggcg tacataccct cccgctgtc    540 ctccaatctt ccggtctcta ctccctgtct tctgttgtca ctgttccatc atcctcactc   600
ggcacaaaaa catatacctg caacgttgat cacaagccaa gtaataccaa agttgataag   660
cgcgtcgaat ccaaatacgg tccccctgc cccccatgtc ccgctccacc tgtggctggt    720
ccctctgttt tccttttttcc ccctaaaccc aaagatacccc tcatgatttc cagaaccccc   780
gaggtcacct gcgtcgtcgt tgatgtaagc caagaagatc ccgaagtcca gttcaattgg   840
tatgtagacg gtgttgaagt ccataatgca aaaacaaaac ccagagagga acagtttaat    900
tcaacctatc gtgtcgttag cgtactcacc gttcttcatc aagactggct caatggaaaa   960
gaatataaat gtaaagttag caacaaaggt ctgcccagtt caatcgaaaa aacaattagc  1020
aaagccaaag ccaacctcg cgaaccccaa gtctatacct tgcccccttc tcaggaagaa   1080
atgaccaaaa accaagtttc actcacatgc ctcgtaaaag gattctatcc atcagacatt  1140
gcagtagaat gggaatctaa cggccaacct gaaataatt acaaaaccac tcctcctgtc   1200
ctcgattctg acggctcttt tttcctttac tccagattga ctgttgataa atcccgctgg  1260
caggaaggta acgttttttc ttgttctgtg atgcacgaag ccctccataa cagattcact  1320
caaaaatctc tttctctctc ccctggcaaa taa                                1353
```

<210> SEQ ID NO 56
<211> LENGTH: 450
<212> TYPE: PRT
<213> ORGANISM: Artificial Sequence
<220> FEATURE:
<223> OTHER INFORMATION: synthetic

<400> SEQUENCE: 56

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr Tyr Tyr Gly Met Asp
            100                 105                 110

Val Trp Gly Gln Gly Thr Thr Val Thr Val Ser Ser Ala Ser Thr Lys
```

```
            115                 120                 125
Gly Pro Ser Val Phe Pro Leu Ala Pro Cys Ser Arg Ser Thr Ser Glu
        130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Lys Thr Tyr Thr Cys Asn
        195                 200                 205

Val Asp His Lys Pro Ser Asn Thr Lys Val Asp Lys Arg Val Glu Ser
        210                 215                 220

Lys Tyr Gly Pro Pro Cys Pro Pro Cys Pro Ala Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn Arg Phe Thr Gln Lys Ser Leu Ser Leu Ser Pro
        435                 440                 445

Gly Lys
    450

<210> SEQ ID NO 57
<211> LENGTH: 208
<212> TYPE: PRT
<213> ORGANISM: Artificial Sequence
<220> FEATURE:
<223> OTHER INFORMATION: hFceR1a ecto-mmH
      aa 1-180: hFceR1a (amino acid V26-Q205) from
      NP_001992
      aa 181-208: Myc-Myc-hexahistidine tag

<400> SEQUENCE: 57

Val Pro Gln Lys Pro Lys Val Ser Leu Asn Pro Pro Trp Asn Arg Ile
```

```
1               5                   10                  15
Phe Lys Gly Glu Asn Val Thr Leu Thr Cys Asn Gly Asn Asn Phe Phe
            20                  25                  30

Glu Val Ser Ser Thr Lys Trp Phe His Asn Gly Ser Leu Ser Glu Glu
            35                  40                  45

Thr Asn Ser Ser Leu Asn Ile Val Asn Ala Lys Phe Glu Asp Ser Gly
        50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
            100                 105                 110

Trp Asp Val Tyr Lys Val Ile Tyr Tyr Lys Asp Gly Glu Ala Leu Lys
            115                 120                 125

Tyr Trp Tyr Glu Asn His Asn Ile Ser Ile Thr Asn Ala Thr Val Glu
        130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln Glu Gln Lys Leu Ile Ser Glu Glu Asp Leu Gly Gly
            180                 185                 190

Glu Gln Lys Leu Ile Ser Glu Glu Asp Leu His His His His His His
            195                 200                 205

<210> SEQ ID NO 58
<211> LENGTH: 208
<212> TYPE: PRT
<213> ORGANISM: Artificial Sequence
<220> FEATURE:
<223> OTHER INFORMATION: mfFceR1a ecto-mmH
      aa 1-180: mf FceR1a (aa V29-Q208; L81W) from
      translation of XM_005541313.2
      aa 181-208: Myc-Myc-hexahistidine tag

<400> SEQUENCE: 58

Val Pro Gln Lys Pro Thr Val Ser Leu Asn Pro Pro Trp Asn Arg Ile
1               5                   10                  15

Phe Lys Gly Glu Asn Val Thr Leu Thr Cys Asn Gly Ser Asn Phe Phe
            20                  25                  30

Glu Val Ser Ser Met Lys Trp Phe His Asn Gly Ser Leu Ser Glu Val
            35                  40                  45

Ala Asn Ser Ser Trp Asn Ile Val Asn Ala Asp Phe Glu Asp Ser Gly
        50                  55                  60

Glu Tyr Lys Cys Gln His Gln Phe Asp Asp Ser Glu Pro Val His
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Ser Trp Arg Asn
            100                 105                 110

Trp Asp Val Tyr Lys Val Ile Tyr Tyr Lys Asp Gly Glu Ala Leu Lys
            115                 120                 125

Tyr Trp Tyr Glu Asn His Asn Ile Ser Ile Thr Asn Ala Thr Val Glu
        130                 135                 140

Asp Ser Gly Thr Tyr Tyr Cys Thr Gly Lys Leu Trp Gln Leu Asp Cys
```

```
145                 150                 155                 160
Glu Ser Glu Pro Leu Asn Ile Thr Val Ile Lys Ala Gln His Asp Lys
                165                 170                 175

Tyr Trp Leu Gln Glu Gln Lys Leu Ile Ser Glu Glu Asp Leu Gly Gly
                180                 185                 190

Glu Gln Lys Leu Ile Ser Glu Glu Asp Leu His His His His His His
                195                 200                 205
```

<210> SEQ ID NO 59
<211> LENGTH: 207
<212> TYPE: PRT
<213> ORGANISM: Artificial Sequence
<220> FEATURE:
<223> OTHER INFORMATION: hCD3 epsilon

<400> SEQUENCE: 59

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
                20                  25                  30

Gln Thr Pro Tyr Lys Val Ser Ile Ser Gly Thr Thr Val Ile Leu Thr
                35                  40                  45

Cys Pro Gln Tyr Pro Gly Ser Glu Ile Leu Trp Gln His Asn Asp Lys
            50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
                100                 105                 110

Tyr Leu Arg Ala Arg Val Cys Glu Asn Cys Met Glu Met Asp Val Met
                115                 120                 125

Ser Val Ala Thr Ile Val Ile Val Asp Ile Cys Ile Thr Gly Gly Leu
            130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
                180                 185                 190

Lys Gly Gln Arg Asp Leu Tyr Ser Gly Leu Asn Gln Arg Arg Ile
                195                 200                 205
```

<210> SEQ ID NO 60
<211> LENGTH: 171
<212> TYPE: PRT
<213> ORGANISM: Artificial Sequence
<220> FEATURE:
<223> OTHER INFORMATION: hCD3 delta

<400> SEQUENCE: 60

```
Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
                20                  25                  30

Val Phe Val Asn Cys Asn Thr Ser Ile Thr Trp Val Glu Gly Thr Val
            35                  40                  45
```

```
Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 61
<211> LENGTH: 164
<212> TYPE: PRT
<213> ORGANISM: Artificial Sequence
<220> FEATURE:
<223> OTHER INFORMATION: hCD3 zeta

<400> SEQUENCE: 61

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr
        50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 62
<211> LENGTH: 182
<212> TYPE: PRT
<213> ORGANISM: Artificial Sequence
<220> FEATURE:
<223> OTHER INFORMATION: hCD3 gamma

<400> SEQUENCE: 62

Met Glu Gln Gly Lys Gly Leu Ala Val Leu Ile Leu Ala Ile Ile Leu
1               5                   10                  15
```

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180

<210> SEQ ID NO 63
<211> LENGTH: 257
<212> TYPE: PRT
<213> ORGANISM: Artificial Sequence
<220> FEATURE:
<223> OTHER INFORMATION: hFceR1a

<400> SEQUENCE: 63

Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Lys Val
                20                  25                  30

Ser Leu Asn Pro Pro Trp Asn Arg Ile Phe Lys Gly Glu Asn Val Thr
            35                  40                  45

Leu Thr Cys Asn Gly Asn Asn Phe Phe Glu Val Ser Ser Thr Lys Trp
        50                  55                  60

Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Gly Trp Arg Asn Trp Asp Val Tyr Lys Val Ile
130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu Pro Leu Asn Ile
            180                 185                 190

-continued

```
Thr Val Ile Lys Ala Pro Arg Glu Lys Tyr Trp Leu Gln Phe Phe Ile
        195                 200                 205

Pro Leu Leu Val Val Ile Leu Phe Ala Val Asp Thr Gly Leu Phe Ile
    210                 215                 220

Ser Thr Gln Gln Gln Val Thr Phe Leu Leu Lys Ile Lys Arg Thr Arg
225                 230                 235                 240

Lys Gly Phe Arg Leu Leu Asn Pro His Pro Lys Pro Asn Pro Lys Asn
                245                 250                 255

Asn
```

ANTI-FC EPSILON-R1 ALPHA (FCεR1α) ANTIBODIES, BISPECIFIC ANTIGEN-BINDING MOLECULES THAT BIND FCεR1α AND CD3, AND USES THEREOF

RELATED APPLICATIONS

This application is related to and claims priority of U.S. Provisional Application No. 62/721,921, filed on Aug. 23, 2018. The entire contents of the foregoing application are expressly incorporated herein by reference.

REFERENCE TO SEQUENCE LISTING

This application incorporates by reference the Sequence Listing submitted in Computer Readable Form as file 10480US01_118003-45303_SL.txt, created on Aug. 21, 2019 and containing 67,335 bytes.

FIELD OF THE INVENTION

The present invention relates to antibodies, and antigen-binding fragments thereof, which are specific for FcεR1α, and methods of use thereof. The present invention also relates to bispecific antigen-binding molecules that bind FcεR1α and CD3, and methods of use thereof.

BACKGROUND

FcεR1 is a high affinity Fc receptor for Immunoglobulin E (IgE), and FcεR1 binds to IgE with an equilibrium dissociation constant ($K_D$) value of about $10^{-10}$ M. FcεR1 receptor crosslinking by allergen-bound IgE leads to cellular degranulation and subsequent allergic response, and the serum level of IgE is positively correlated with FcεR1.

Human FcεR1 is expressed in mast cells, basophils, monocytes, macrophages, mDCs, pDCs, Langerhans cells, eosinophils and platelets. Mast cells and basophils are innate effector cells that play a role in allergy and anaphylaxis via allergen mediated crosslinking of the IgE receptor, FcεR1α. Other roles include wound healing and mucosal immunity.

There are two types of human multimeric cell surface FcεR1 receptors, the tetrameric form and the trimeric form. The tetrameric human FcεR1 comprises an α chain, a β chain, and a homodimer of γ chains ($\alpha\beta\gamma_2$), and the trimeric human FcεR1 comprises an α chain and a homodimer of γ chains ($\alpha\gamma_2$). The α-chain of FcεR1 binds to a single IgE antibody molecule, while there is no reported role for β- and γ-chains in ligand binding.

Human FcεR1 binds to both human and murine IgE, and interleukin-4 (IL-4) enhances the expression of the α-chain in humans. In contrast, murine FcεR1 only has the tetrameric $\alpha\beta\gamma_2$ isoform and is expressed in mast cells and basophils. IL-4 does not enhance the expression of the α-chain of murine FcεR1.

CD3 is a homodimeric or heterodimeric antigen expressed on T cells in association with the T cell receptor complex (TCR) and is required for T cell activation. Functional CD3 is formed from the dimeric association of two of four different chains: epsilon, zeta, delta and gamma. The CD3 dimeric arrangements include gamma/epsilon, delta/epsilon, and zeta/zeta. Antibodies against CD3 have been shown to cluster CD3 on T cells, thereby causing T cell activation in a manner similar to the engagement of the TCR by peptide-loaded MHC molecules. Thus, anti-CD3 antibodies have been proposed for therapeutic purposes involving the activation of T cells.

Antigen-binding molecules that target FcεR1α, as well as bispecific antigen-binding molecules that bind both FcεR1α and CD3 would be useful in therapeutic settings in which specific targeting and T cell-mediated killing of cells that express FcεR1α is desired.

BRIEF SUMMARY OF THE INVENTION

In a first aspect, the present invention provides antibodies and antigen-binding fragments thereof that bind to human FcεR1α. The antibodies according to this aspect are useful, inter alia, for targeting cells expressing FcεR1α. The present invention also provides bispecific antibodies and antigen-binding fragments thereof that bind human FcεR1α and human CD3. The bispecific antibodies according to this aspect are useful, inter alia, for targeting T cells expressing CD3, and for stimulating T cell activation, e.g., under circumstances where T cell-mediated killing of cells expressing FcεR1α is beneficial or desirable. For example, the bispecific antibodies can direct CD3-mediated T cell activation to specific FcεR1α-expressing cells, such as mast cells or basophils.

Exemplary anti-FcεR1α antibodies of the present invention are listed in Tables 1 and 2 herein. Table 1 sets forth the amino acid sequence identifiers of the heavy chain variable regions (HCVRs) and light chain variable regions (LCVRs), as well as heavy chain complementarity determining regions (HCDR1, HCDR2 and HCDR3), light chain complementarity determining regions (LCDR1, LCDR2 and LCDR3), heavy chain (HC), and light chain (LC) of the exemplary anti-FcεR1α antibodies. Table 2 sets forth the sequence identifiers of the nucleic acid molecules encoding the HCVRs, LCVRs, HCDR1, HCDR2 HCDR3, LCDR1, LCDR2, LCDR3, HC and LC of the exemplary anti-FcεR1α antibodies.

The present invention provides antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-FcεR1α antibodies listed in Table 1. In certain embodiments, the HCVR/LCVR amino acid sequence pair is of SEQ ID NOs: 2/26, 10/26, or 18/26 (e.g., mAb17110, mAb17111, or mAb17112)

The present invention also provides antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-FcεR1α antibodies listed in Table 1. In certain embodiments, the HCDR3/LCDR3 amino acid sequence pair is of SEQ ID NOs: 8/32, 16/32, or 24/32 (e.g., mAb17110, mAb17111, or mAb17112).

The present invention also provides antibodies, or antigen-binding fragments thereof, comprising a set of six CDRs (i.e., HCDR1-HCDR2-HCDR3-LCDR1-LCDR2-LCDR3) contained within any of the exemplary anti-FcεR1α antibodies listed in Table 1. In certain embodiments, the HCDR1-HCDR2-HCDR3-LCDR1-LCDR2-LCDR3 amino acid sequences set is selected from the group consisting of SEQ ID NOs: 4-6-8-28-30-32, 12-14-16-28-30-32, or 20-22-24-28-30-32 (e.g., mAb17110, mAb17111, or mAb17112).

In a related embodiment, the present invention provides antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary anti-FcεR1α antibodies listed in Table 1. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair of SEQ ID NOs: 2/26, 10/26, or 18/26 (e.g., mAb17110, mAb17111, or mAb17112). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention also provides nucleic acid molecules encoding anti-FcεR1α antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-FcεR1α antibodies listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-FcεR1α antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-FcεR1α antibody listed in Table 1.

The present invention also provides recombinant expression vectors capable of expressing a polypeptide comprising a heavy or light chain variable region of an anti-FcεR1α antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

The present invention includes anti-FcεR1α antibodies having a modified glycosylation pattern. In some embodiments, modification to remove undesirable glycosylation sites may be useful, or an antibody lacking a fructose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides a pharmaceutical composition comprising a recombinant human antibody or fragment thereof which specifically binds FcεR1α and a pharmaceutically acceptable carrier. In a related aspect, the invention features a composition which is a combination of an anti-FcεR1α antibody and a second therapeutic agent. In one embodiment, the second therapeutic agent is any agent that is advantageously combined with an anti-FcεR1α antibody. Additional combination therapies and co-formulations involving the anti-FcεR1α antibodies of the present invention are disclosed elsewhere herein.

In another aspect, the invention provides therapeutic methods for targeting/killing FcεR1α-expressing cells (e.g., mast cells, or basophils) using an anti-FcεR1α antibody of the invention, wherein the therapeutic methods comprise administering a therapeutically effective amount of a pharmaceutical composition comprising an anti-FcεR1α antibody of the invention to a subject in need thereof. In some cases, the anti-FcεR1α antibodies (or antigen-binding fragments thereof) can be used for treating allergy, or may be modified to be more cytotoxic by methods, including but not limited to, modified Fc domains to increase ADCC (see e.g. Shield et al. (2002) JBC 277:26733), radioimmunotherapy, antibody-drug conjugates, or other methods for increasing the efficiency of FcεR1α expressing cells killing.

The present invention also includes the use of an anti-FcεR1α antibody of the invention in the manufacture of a medicament for the treatment of a disease or disorder (e.g., allergy) related to or caused by FcεR1α-expressing cells.

In yet another aspect, the invention provides monospecific anti-FcεR1α antibodies for diagnostic applications, such as, e.g., imaging reagents.

In yet another aspect, the invention provides therapeutic methods for stimulating T cell activation using an anti-CD3 antibody or antigen-binding portion of an antibody of the invention, wherein the therapeutic methods comprise administering a therapeutically effective amount of a pharmaceutical composition comprising an antibody of the present invention.

In another aspect, the present invention provides an isolated antibody or antigen-binding fragment thereof that binds human FcεR1α or binds cynomolgus (*Macaca fascicularis*) FcεR1α with a binding dissociation equilibrium constant ($K_D$) of less than about 250 nM as measured in a surface plasmon resonance assay at 25° C. In yet another aspect, the present invention provides an isolated antibody or antigen-binding fragment thereof that binds human FcεR1α with a dissociative half-life (t½) of greater than about 0.54 minute or binds cynomolgus FcεR1α with a dissociative half-life (t½) of greater than about 0.6 minute as measured in a surface plasmon resonance assay at 25° C.

The invention further provides an antibody or antigen-binding fragment that competes for binding to human FcεR1α with a reference antibody comprising an HCVR/LCVR amino acid sequence pair as set forth in Table 1. In another aspect, the invention provides an antibody or antigen-binding fragment that competes for binding to human FcεR1α with a reference antibody comprising an HCVR/

LCVR amino acid sequence pair selected from the group consisting of SEQ ID NOs: 2/26; 10/26; and 18/26.

The invention furthermore provides an antibody or antigen-binding fragment, wherein the antibody or antigen-binding fragment thereof binds to the same epitope on human FcεR1α as a reference antibody comprising an HCVR/LCVR amino acid sequence pair as set forth in Table 1. In another aspect, the antibody or antigen-binding fragment binds to the same epitope on human FcεR1α as a reference antibody comprising an HCVR/LCVR amino acid sequence pair selected from the group consisting of SEQ ID NOs: 2/26; 10/26, and 18/26.

The invention further provides an isolated antibody or antigen-binding fragment thereof that binds human FcεR1α, wherein the antibody or antigen-binding fragment comprises: the complementarity determining regions (CDRs) of a heavy chain variable region (HCVR) having an amino acid sequence as set forth in Table 1; and the CDRs of a light chain variable region (LCVR) having an amino acid sequence as set forth in Table 1. In another aspect, the isolated antibody or antigen-binding fragment comprises the heavy and light chain CDRs of an HCVR/LCVR amino acid sequence pair selected from the group consisting of: 2/26; 10/26; and 18/26. In yet another aspect, the isolated antibody or antigen-binding fragment comprises HCDR1-HCDR2-HCDR3-LCDR1-LCDR2-LCDR3 domains, respectively, selected from the group consisting of: SEQ ID NOs: 4-6-8-28-30-32; 12-14-16-28-30-32; and 20-22-24-28-30-32

In another aspect, the invention provides an isolated antibody or antigen-binding fragment thereof that binds human FcεR1α, wherein the antibody or antigen-binding fragment comprises: (a) a heavy chain variable region (HCVR) having an amino acid sequence selected from the group consisting of SEQ ID NOs: 2, 10, and 18; and (b) a light chain variable region (LCVR) having an amino acid sequence SEQ ID NO: 26. In a further aspect, the isolated antibody or antigen-binding fragment an HCVR/LCVR amino acid sequence pair selected from the group consisting of: SEQ ID NOs: 2/26; 10/26; and 18/26.

According to another aspect, the present invention provides bispecific antigen-binding molecules (e.g., antibodies) that bind FcεR1α and CD3. Such bispecific antigen-binding molecules are also referred to herein as "anti-FcεR1α/anti-CD3 bispecific molecules," "anti-CD3/anti-FcεR1α bispecific molecules," "anti-FcεR1α×CD3," "anti-CD3× FcεR1α," or "FcεR1α×CD3 bsAbs." The anti-FcεR1α portion of the anti-FcεR1α/anti-CD3 bispecific molecule is useful for targeting cells that express FcεR1α (e.g., mast cells or basophils), and the anti-CD3 portion of the bispecific molecule is useful for activating T-cells. The simultaneous binding of FcεR1α on a mast cells or basophils and CD3 on a T-cell facilitates directed killing (cell lysis) of the targeted mast cells or basophils by the activated T-cell. The anti-FcεR1α/anti-CD3 bispecific molecules of the invention are therefore useful, inter alia, for treating diseases and disorders related to or caused by FcεR1α-expressing cells (e.g., allergy).

The bispecific antigen-binding molecules according to this aspect of the present invention comprise a first antigen-binding domain that specifically binds human CD3, and a second antigen-binding domain that specifically binds FcεR1α. The present invention includes anti-FcεR1α/anti-CD3 bispecific molecules (e.g., bispecific antibodies) wherein each antigen-binding domain comprises a heavy chain variable region (HCVR) paired with a light chain variable region (LCVR). In certain exemplary embodiments of the invention, the anti-CD3 antigen-binding domain and the anti-FcεR1α antigen binding domain each comprise different, distinct HCVRs paired with a common LCVR. For example, as illustrated in Example 1 herein, bispecific antibodies were constructed comprising a first antigen-binding domain that specifically binds CD3, wherein the first antigen-binding domain comprises an HCVR and an LCVR, each derived from an anti-CD3 antibody; and a second antigen-binding domain that specifically binds FcεR1α, wherein the second antigen-binding domain comprises an HCVR derived from an anti-FcεR1α antibody paired with the same LCVR. In such embodiments, the first and second antigen-binding domains comprise distinct anti-CD3 and anti-FcεR1α HCVRs but share a common LCVR. The amino acid sequence of this LCVR is shown, e.g., in SEQ ID NO: 26, and the amino acid sequences of the corresponding CDRs (i.e., LCDR1-LCDR2-LCDR3) are shown in SEQ ID NOs: 28, 30, and 32, respectively. Genetically modified mice can be used to produce fully human bispecific antigen-binding molecules comprising two different heavy chains that associate with an identical light chain that comprises a variable domain derived from one of two different human light chain variable region gene segments. Alternatively, variable heavy chains may be paired with one common light chain and expressed recombinantly in host cells. As such, the antibodies of the invention can comprise immunoglobulin heavy chains associated with a single rearranged light chain. In some embodiments, the light chain comprises a variable domain derived from a human VK1-39 gene segment or a VK3-20 gene segment. In other embodiments, the light chain comprises a variable domain derived from a human VK1-39 gene segment rearranged with a human JK5 or a human JK1 gene segment (WO 2017/053856, herein incorporated by reference).

The present invention provides anti-CD3/anti-FcεR1α bispecific molecules, wherein the first antigen-binding domain that specifically binds CD3 comprises any of the HCVR amino acid sequences, any of the LCVR amino acid sequences, any of the HCVR/LCVR amino acid sequence pairs, any of the heavy chain CDR1-CDR2-CDR3 amino acid sequences, or any of the light chain CDR1-CDR2-CDR3 amino acid sequences as set forth in US publication 2014/0088295 published Mar. 27, 2014 and WO 2018/067331 published Apr. 12, 2018.

In addition, the present invention provides anti-CD3/anti-FcεR1α bispecific molecules, wherein the first antigen-binding domain that specifically binds CD3 comprises any of the HCVR amino acid sequences as set forth in Table 3 herein. The first antigen-binding domain that specifically binds CD3 may also comprise any of the LCVR amino acid sequences as set forth in Tables 1, and 3 herein. The present invention also provides anti-CD3/anti-FcεR1α bispecific molecules, wherein the first antigen-binding domain that specifically binds CD3 comprises any of the heavy chain CDR1-CDR2-CDR3 amino acid sequences as set forth in Table 3, and/or any of the light chain CDR1-CDR2-CDR3 amino acid sequences as set forth in Tables 1, and 3 herein.

According to certain embodiments, the present invention provides anti-CD3/anti-FcεR1α bispecific molecules, wherein the first antigen-binding domain that specifically binds CD3 comprises a heavy chain variable region (HCVR) having an amino acid sequence as set forth in Table 1 herein or a substantially similar sequence thereof having at least 90%, at least 95%, at least 98% or at least 99% sequence identity.

The present invention also provides anti-CD3/anti-FcεR1α bispecific molecules, wherein the first antigen-binding domain that specifically binds CD3 comprises a light chain variable region (LCVR) having an amino acid sequence as set forth in Tables 1, and 3 herein, or a substantially similar sequence thereof having at least 90%, at least 95%, at least 98% or at least 99% sequence identity.

The present invention also provides anti-CD3/anti-FcεR1α bispecific molecules, wherein the first antigen-binding domain that specifically binds CD3 comprises an HCVR and LCVR (HCVR/LCVR) amino acid sequence pair as set forth in Table 3 herein.

The present invention also provides anti-CD3/anti-FcεR1α bispecific molecules, wherein the first antigen-binding domain that specifically binds CD3 comprises a heavy chain CDR3 (HCDR3) domain having an amino acid sequence as set forth in Table 3 herein, or a substantially similar sequence thereto having at least 90%, at least 95%, at least 98% or at least 99% sequence identity; and a light chain CDR3 (LCDR3) domain having an amino acid sequence as set forth in Tables 1, and 3 herein, or a substantially similar sequence thereof having at least 90%, at least 95%, at least 98% or at least 99% sequence identity.

In certain embodiments, the first antigen-binding domain that specifically binds CD3 comprises an HCDR3/LCDR3 amino acid sequence pair as set forth in Table 3 herein.

The present invention also provides anti-CD3/anti-FcεR1α bispecific antigen-binding molecules, wherein the first antigen-binding domain that specifically binds CD3 comprises a heavy chain CDR1 (HCDR1) domain having an amino acid as set forth in Table 3 herein, or a substantially similar sequence thereof having at least 90%, at least 95%, at least 98% or at least 99% sequence identity; a heavy chain CDR2 (HCDR2) domain having an amino acid as set forth in Table 3, or a substantially similar sequence thereof having at least 90%, at least 95%, at least 98% or at least 99% sequence identity; a heavy chain CDR3 (HCDR3) domain having an amino acid as set forth in Table 3, or a substantially similar sequence thereof having at least 90%, at least 95%, at least 98% or at least 99% sequence identity; a light chain CDR1 (LCDR1) domain having an amino acid sequence as set forth in Tables 1, and 3 herein, or a substantially similar sequence thereof having at least 90%, at least 95%, at least 98% or at least 99% sequence identity; a light chain CDR2 (LCDR2) domain having an amino acid sequence as set forth in Tables 1, and 3 herein, or a substantially similar sequence thereof having at least 90%, at least 95%, at least 98% or at least 99% sequence identity; and a light chain CDR3 (LCDR3) domain having an amino acid sequence as set forth in Tables 1, and 3 herein, or a substantially similar sequence thereof having at least 90%, at least 95%, at least 98% or at least 99% sequence identity.

Certain non-limiting, exemplary anti-CD3/anti-FcεR1α bispecific antigen-binding molecules of the invention include a first antigen-binding domain that specifically binds CD3 comprising HCDR1-HCDR2-HCDR3-LCDR1-LCDR2-LCDR3 domains, respectively, having the amino acid sequences as set forth in Table 3 herein.

The present invention further provides a bispecific antigen-binding molecule, wherein the first antigen-binding domain that specifically binds human CD3 comprises heavy chain complementarity determining regions (HCDR1, HCDR2 and HCDR3) from a heavy chain variable region (HCVR) comprising an amino acid sequence as set forth in Table 3 and light chain complementarity determining regions (LCDR1, LCDR2 and LCDR3) from a light chain variable region (LCVR) comprising an amino acid sequence as set forth in Tables 1, and 3.

In another aspect, the invention provides a bispecific antigen-binding molecule wherein the first antigen-binding domain that specifically binds human CD3 comprises heavy chain complementarity determining regions (HCDR1, HCDR2 and HCDR3) from a heavy chain variable region (HCVR) comprising an amino acid sequence of SEQ ID NO: 42, and light chain complementarity determining regions (LCDR1, LCDR2 and LCDR3) from a light chain variable region (LCVR) comprising an amino acid sequence of SEQ ID NO: 26.

The invention further provides a bispecific antigen-binding molecule, wherein the first antigen-binding domain that specifically binds human CD3 comprises HCDR1-HCDR2-HCDR3-LCDR1-LCDR2-LCDR3 comprising the amino acid sequences of SEQ ID Nos: 44-46-48-28-30-32.

In a further aspect, the invention provides a bispecific antigen-binding molecule, wherein the first antigen-binding domain that specifically binds human CD3 comprises the heavy and light chain CDRs of an HCVR/LCVR amino acid sequence pair of SEQ ID NO: 42/26.

In more embodiments, exemplary anti-CD3/anti-FcεR1α bispecific antigen-binding molecules of the invention include a bispecific antigen-binding molecule wherein the first antigen-binding domain that specifically binds human CD3 comprises an HCVR comprising HCDR1-HCDR2-HCDR3 having the amino acid sequences of SEQ ID NOs: 44-46-48.

The present invention also provides anti-CD3/anti-FcεR1α bispecific molecules, wherein the second antigen-binding domain that specifically binds FcεR1α comprises a heavy chain variable region (HCVR) having the amino acid sequence selected from the group consisting of SEQ ID NOs: 2, 10, and 18, or a substantially similar sequence thereof having at least 90%, at least 95%, at least 98% or at least 99% sequence identity.

The present invention also provides anti-CD3/anti-FcεR1α bispecific molecules, wherein the second antigen-binding domain that specifically binds FcεR1α comprises a light chain variable region (LCVR) having the amino acid sequence of SEQ ID NO: 26, or a substantially similar sequence thereof having at least 90%, at least 95%, at least 98% or at least 99% sequence identity.

The present invention also provides anti-CD3/anti-FcεR1α bispecific molecules, wherein the second antigen-binding domain that specifically binds FcεR1α comprises an HCVR and LCVR (HCVR/LCVR) amino acid sequence pair selected from the group consisting of SEQ ID NOs: 2/26, 10/26, and 18/26.

The present invention also provides anti-CD3/anti-FcεR1α bispecific molecules, wherein the second antigen-binding domain that specifically binds FcεR1α comprises a heavy chain CDR3 (HCDR3) domain having an amino acid sequence selected from the group consisting of SEQ ID NOs: 8, 16, and 24, or a substantially similar sequence thereto having at least 90%, at least 95%, at least 98% or at least 99% sequence identity; and a light chain CDR3 (LCDR3) domain having an amino acid sequence of SEQ ID NO: 32, or a substantially similar sequence thereof having at least 90%, at least 95%, at least 98% or at least 99% sequence identity.

In certain embodiments, the second antigen-binding domain that specifically binds FcεR1α comprises an HCDR3/LCDR3 amino acid sequence pair selected from the group consisting of SEQ ID NOs: 8/32, 16/32, and 24/32.

The present invention also provides anti-CD3/anti-FcεR1α bispecific antigen-binding molecules, wherein the second antigen-binding domain that specifically binds FcεR1α comprises a heavy chain CDR1 (HCDR1) domain having an amino acid sequence selected from the group consisting of SEQ ID NOs: 4, 12, and 20, or a substantially similar sequence thereof having at least 90%, at least 95%, at least 98% or at least 99% sequence identity; a heavy chain CDR2 (HCDR2) domain having an amino acid sequence selected from the group consisting of SEQ ID NOs: 6, 14, and 22, or a substantially similar sequence thereof having at least 90%, at least 95%, at least 98% or at least 99% sequence identity; a heavy chain CDR3 (HCDR3) domain having an amino acid sequence selected from the group consisting of SEQ ID NOs: 8, 16, and 24, or a substantially similar sequence thereof having at least 90%, at least 95%, at least 98% or at least 99% sequence identity; a light chain CDR1 (LCDR1) domain having an amino acid sequence of SEQ ID NOs: 28, or a substantially similar sequence thereof having at least 90%, at least 95%, at least 98% or at least 99% sequence identity; and a light chain CDR2 (LCDR2) domain having an amino acid sequence of SEQ ID NO: 30, or a substantially similar sequence thereof having at least 90%, at least 95%, at least 98% or at least 99% sequence identity; and a light chain CDR3 (LCDR3) domain having an amino acid sequence of SEQ ID NOs: 32, or a substantially similar sequence thereof having at least 90%, at least 95%, at least 98% or at least 99% sequence identity.

Certain non-limiting, exemplary anti-CD3/anti-FcεR1α bispecific antigen-binding molecules of the invention include a second antigen-binding domain that specifically binds FcεR1α comprising HCDR1-HCDR2-HCDR3-LCDR1-LCDR2-LCDR3 domains, respectively, having the amino acid sequences selected from the group consisting of: SEQ ID NOs: 4-6-8-28-30-32, 12-14-16-28-30-32, and 20-22-24-28-30-32.

In a related embodiment, the invention includes anti-CD3/anti-FcεR1α bispecific antigen-binding molecules wherein the second antigen-binding domain that specifically binds FcεR1α comprises the heavy and light chain CDR domains contained within heavy and light chain variable region (HCVR/LCVR) sequences selected from the group consisting of SEQ ID NOs: 2/26, 10/26, and 18/26.

In another aspect, the invention provides a bispecific antigen-binding molecule comprising: (a) a first antigen-binding domain that comprises three heavy chain complementarity determining regions HCDR1, HCDR2 and HCDR3, respectively, comprising the amino acid sequences of SEQ ID NOs: 44, 46 and 48, and three light chain complementarity determining regions LCDR1, LCDR2 and LCDR3, respectively, comprising the amino acid sequences of SEQ ID NOs: 28, 30 and 32, wherein the first antigen-binding domain specifically binds human CD3; and (b) a second antigen-binding domain that comprises three heavy chain complementarity determining regions (HCDR1, HCDR2 and HCDR3) and three light chain complementarity determining regions (LCDR1, LCDR2 and LCDR3); wherein HCDR1 comprises an amino acid sequence selected from the group consisting of: SEQ ID NOs: 4, 12, and 20; HCDR2 comprises an amino acid sequence selected from the group consisting of SEQ ID NOs: 6, 14, and 22; HCDR3 comprises an amino acid sequence selected from the group consisting of SEQ ID NO: 8, 16, and 24; LCDR1 comprises an amino acid sequence of SEQ ID NO: 28; LCDR2 comprises an amino acid sequence of SEQ ID NO: 30; and LCDR3 comprises an amino acid sequence of SEQ ID NO: 32, wherein the second antigen-binding arm specifically binds human FcεR1α.

In another aspect, the invention provides a bispecific antigen-binding molecule comprising a first antigen-binding domain that binds human CD3 and a second antigen-binding domain that binds human FcεR1α, wherein the second antigen-binding domain is derived from the antibody or antigen-binding fragment of any one of the anti-FcεR1α antibodies of the invention. In a further aspect, the invention provides a bispecific antigen-binding molecule comprising a first antigen-binding domain that specifically binds human CD3, and a second antigen-binding domain that specifically binds human FcεR1α.

The invention further provides a bispecific antigen-binding molecule which binds human cells expressing human CD3. In another aspect, the bispecific antigen-binding molecule binds human cells expressing human FcεR1α and/or cells expressing cynomolgus FcεR1α.

In another aspect the invention provides a bispecific antigen-binding molecule which inhibits allergic reaction in a subject (e.g., mice) expressing human FcεR1α. The invention further provides bispecific antigen-binding molecules which deplete basophils or other FcεR1α-expressing cells in a subject (e.g., mice) expressing human FcεR1α.

In another aspect the invention provides a bispecific antigen-binding molecule comprising a second antigen-binding domain that specifically binds a target cell expressing human FcεR1α with a binding ratio greater than 200 in the presence or absence of IgE or binds a target cell expressing cynomolgus FcεR1α with a binding ratio greater than 140 in the presence of absence of IgE, wherein such binding ratio is measured in an in vitro FACS binding assay.

In some embodiments, the antigen-binding molecule induces T cell-mediated killing of FcεR1α-expressing with an $EC_{50}$ value of less than about 20 nM, as measured in an in vitro T cell-mediated cell killing assay, for example, where the FcεR1α expressing cells are basophils.

In some applications, the second antigen-binding domain binds human or cynomolgus FcεR1α with a $K_D$ value of less than about 467 nM, as measured in an in vitro surface plasmon resonance binding assay at 25° C. In some instances, the second antigen-binding domain binds each of human FcεR1α and cynomolgus FcεR1α with an $K_D$ value of less than about 450 nM, less than about 400 nM, less than about 350 nM, less than about 300 nM, less than about 250 nM, less than about 200 nM, less about 150 nM, less than about 100 nM, or less than about 50 nM.

In certain embodiments, anti-FcεR1α antibodies of the invention, antigen-binding fragments and bispecific antibodies thereof were made by replacing amino acid residues of a parental in a stepwise manner based on differences between the germline sequence and the parental antibody sequence.

In another aspect, the present invention provides an isolated bispecific antigen-binding molecule that competes for binding to FcεR1α, or binds to the same epitope on FcεR1α as a reference antibody, wherein the reference antibody comprises a first antigen-binding domain comprising an HCVR/LCVR pair comprising the amino acid sequences of SEQ ID NOs: 42/26, and a second antigen-binding domain comprising an HCVR/LCVR pair comprising the amino acid sequences of SEQ ID NOs: 2/26, 10/26 or 18/26.

In another aspect, the present invention provides an isolated bispecific antigen-binding molecule that competes for binding to human CD3, or binds to the same epitope on human CD3 as a reference antibody, wherein the reference antibody comprises a first antigen-binding domain comprising an HCVR/LCVR pair comprising the amino acid sequences of SEQ ID NOs: 42/26, and a second antigen-binding domain comprising an HCVR/LCVR pair comprising the amino acid sequences of SEQ ID NOs: 2/26, 10/26 or 18/26.

Any of the bispecific antigen-binding molecules discussed above or herein may be a bispecific antibody. In some embodiments, the bispecific antibody comprises a human IgG heavy chain constant region. In one embodiment, the human IgG heavy chain constant region is isotype IgG1. In one embodiment, the human IgG heavy chain constant region is isotype IgG4. In various embodiments, the bispecific antibody comprises a chimeric hinge that reduces Fcγ receptor binding relative to a wild-type hinge of the same isotype.

The present invention also provides antibodies, or antigen-binding fragments thereof, comprising a heavy chain (HC) and a light chain (LC) amino acid sequence pair (HC/LC) comprising any of the HC amino acid sequences listed in Table 1 paired with any of the LC amino acid sequences listed in Table 1. According to certain embodiments, the present invention provides antibodies, or antigen-binding fragments thereof, comprising an HC/LC amino acid sequence pair contained within any of the exemplary anti-FcεR1α antibodies listed in Table 1. In certain embodiments, the HC/LC amino acid sequence pair is selected from the group consisting of SEQ ID NOs: 34/40, 36/40, and 38/40.

The present invention also provides bispecific antibodies, or antigen-binding fragments thereof comprising a first heavy chain, a second heavy chain and a common light chain comprising any of the HC or LC amino acid sequences listed in Table 7. In certain embodiments, the bispecific antibodies comprise a first HC comprising an amino acid sequence of SEQ ID NO: 56; a second HC comprising an amino acid sequence selected from the group consisting of SEQ ID NOs: 50, 52 and 54; and a common light chain comprising the amino acid sequence of SEQ ID NO: 40.

In one aspect, the invention provides a pharmaceutical composition comprising an anti-FcεR1α antigen-binding molecule or anti-FcεR1α/anti-CD3 bispecific antigen-binding molecule and a pharmaceutically acceptable carrier or diluent. The invention further provides a method for treating an FcεR1α-related disease, allergy or an IgE-related disease in a subject, the method comprising administering to the subject the pharmaceutical composition comprising an anti-FcεR1α antigen-binding molecule or anti-FcεR1α/anti-CD3 bispecific antigen-binding molecule and a pharmaceutically acceptable carrier or diluent. In some embodiments, the allergy or other IgE-related diseases are selected from the group consisting of allergic asthma, allergic rhinitis, hay fever, anaphylaxis, atopic dermatitis, chronic urticarial, food allergy, perennial allergy, drug allergy, and pollen allergy. In one embodiment, the allery is severe allergy. In some cases, the allergy leads to anaphylaxis. In certain embodiments, the FcεR1α-related disease comprises severe allergy, mast cell activation disorder or mastocytosis. In certain embodiments, the method for treating allergy comprises administering to the subject the pharmaceutical composition comprising an anti-FcεR1α antigen-binding molecule or anti-FcεR1α/anti-CD3 bispecific antigen-binding molecule at a certain dose, as described elsewhere herein.

In another aspect, the present invention provides nucleic acid molecules encoding any of the HCVR, LCVR or CDR sequences of the anti-FcεR1α, and anti-CD3/anti-FcεR1α bispecific antigen-binding molecules disclosed herein, including nucleic acid molecules comprising the polynucleotide sequences as set forth in Tables 2, and 4 herein, as well as nucleic acid molecules comprising two or more of the polynucleotide sequences as set forth in Tables 2, and 4 in any functional combination or arrangement thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

The present invention provides nucleic acid molecules encoding any of the heavy chain amino acid sequences listed in Table 7. The present invention also provides nucleic acid molecules encoding any of the light chain amino acid sequences listed in Table 7.

The present invention includes anti-CD3/anti-FcεR1α bispecific antigen-binding molecules wherein any of the aforementioned antigen-binding domains that specifically bind CD3 are combined, connected or otherwise associated with any of the aforementioned antigen-binding domains that specifically bind FcεR1α to form a bispecific antigen-binding molecule that binds CD3 and FcεR1α.

The present invention includes anti-CD3/anti-FcεR1α bispecific antigen-binding molecules having a modified glycosylation pattern. In some applications, modification to remove undesirable glycosylation sites may be useful, or an antibody lacking a fructose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides a pharmaceutical composition comprising an anti-CD3/anti-FcεR1α bispecific antigen-binding molecule as disclosed herein and a pharmaceutically acceptable carrier. In a related aspect, the invention features a composition which is a combination of an anti-CD3/anti-FcεR1α bispecific antigen-binding molecule and a second therapeutic agent. In one embodiment, the second therapeutic agent is any agent that is advantageously combined with an anti-CD3/anti-FcεR1α bispecific antigen-binding molecule.

Exemplary agents that may be advantageously combined with an anti-CD3/anti-FcεR1α bispecific antigen-binding molecule are discussed in detail elsewhere herein.

In yet another aspect, the invention provides therapeutic methods for targeting/ablating cells expressing FcεR1α using an anti-CD3/anti-FcεR1α bispecific antigen-binding molecule of the invention, wherein the therapeutic methods comprise administering a therapeutically effective amount of a pharmaceutical composition comprising an anti-CD3/anti-FcεR1α bispecific antigen-binding molecule of the invention to a subject in need thereof. The antibody or fragment thereof may be administered sub-cutaneously, intravenously, intradermally, intraperitoneally, orally or intramuscularly. In certain embodiments, an antibody of the invention is administered at a dose of about 0.001 mg/kg body weight to about 200 mg/kg body weight of the subject. In certain embodiments, an antibody of the invention is administered at a dose comprising between 1 mg to 2500 mg of the antibody to a subject in need thereof.

The present invention also includes the use of an anti-CD3/anti-FcεR1α bispecific antigen-binding molecule of the invention in the manufacture of a medicament for the treatment of a disease or disorder related to or caused by FcεR1α-expressing cells.

Other embodiments will become apparent from a review of the ensuing detailed description.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expression "CD3," as used herein, refers to an antigen which is expressed on T cells as part of the multimolecular T cell receptor (TCR) and which consists of a homodimer or heterodimer formed from the association of two of four receptor chains: CD3-epsilon, CD3-delta, CD3-zeta, and CD3-gamma. All references to proteins, polypeptides and protein fragments herein are intended to refer to the human version of the respective protein, polypeptide or protein fragment unless explicitly specified as being from a non-human species. Thus, the expression "CD3" means human CD3 unless specified as being from a non-human species, e.g., "mouse CD3," "monkey CD3," etc. Human CD3-epsilon comprises the amino acid sequence set forth as SEQ ID NO: 59; human CD3-delta comprises the amino acid sequence set forth as SEQ ID NO: 60; CD3-zeta comprises the amino acid sequence set forth as SEQ ID NO: 61; and CD3-gamma comprises the amino acid sequence set forth as SEQ ID NO: 62.

As used herein, "an antibody that binds CD3" or an "anti-CD3 antibody" includes antibodies and antigen-binding fragments thereof that specifically recognize a single CD3 subunit (e.g., epsilon, delta, gamma or zeta), as well as antibodies and antigen-binding fragments thereof that specifically recognize a dimeric complex of two CD3 subunits (e.g., gamma/epsilon, delta/epsilon, and zeta/zeta CD3 dimers). The antibodies and antigen-binding fragments of the present invention may bind soluble CD3 and/or cell surface expressed CD3. Soluble CD3 includes natural CD3 proteins as well as recombinant CD3 protein variants such as, e.g., monomeric and dimeric CD3 constructs, that lack a transmembrane domain or are otherwise unassociated with a cell membrane.

As used herein, the expression "cell surface-expressed CD3" means one or more CD3 protein(s) that is/are expressed on the surface of a cell in vitro or in vivo, such that at least a portion of a CD3 protein is exposed to the extracellular side of the cell membrane and is accessible to an antigen-binding portion of an antibody. "Cell surface-expressed CD3" includes CD3 proteins contained within the context of a functional T cell receptor in the membrane of a cell. The expression "cell surface-expressed CD3" includes CD3 protein expressed as part of a homodimer or heterodimer on the surface of a cell (e.g., gamma/epsilon, delta/epsilon, and zeta/zeta CD3 dimers). The expression, "cell surface-expressed CD3" also includes a CD3 chain (e.g., CD3-epsilon, CD3-delta or CD3-gamma) that is expressed by itself, without other CD3 chain types, on the surface of a cell. A "cell surface-expressed CD3" can comprise or consist of a CD3 protein expressed on the surface of a cell which normally expresses CD3 protein. Alternatively, "cell surface-expressed CD3" can comprise or consist of CD3 protein expressed on the surface of a cell that normally does not express human CD3 on its surface but has been artificially engineered to express CD3 on its surface.

The expression "FcεR1α," as used herein, refers to an α-chain of the high affinity Fc receptor (FcεR1) for IgE. FcεR1α is responsible for the binding of IgE to FcεR1. FcεR1α is expressed in mast cells, basophils, monocytes, macrophages, mDCs, pDCs, Langerhans cells, eosinophils and platelets. The amino acid sequence of human FcεR1α is set forth as SEQ ID NO: 63. The term "FcεR1α" includes recombinant FcεR1α protein or a fragment thereof. The term also encompasses FcεR1α protein or a fragment thereof coupled to, for example, histidine tag, mouse or human Fc, or a signal sequence such as ROR1 (for example, SEQ ID NOs: 57 or 58).

As used herein, "an antibody that binds FcεR1α" or an "anti-FcεR1α antibody" includes antibodies and antigen-binding fragments thereof that specifically recognize FcεR1α.

As used herein, the term "disease or disorder associated with expression of FcεR1α" includes any disease or disorder in which inhibition of expression and/or activity (e.g., signaling) of FcεR1α and/or ablation of cells expressing FcεR1α is expected to alleviate symptoms and/or progression of the disorder. For example, such diseases and disorders include, but are not limited to mast cell activation disorders, mastocytosis, and allergy, including but not limited to food allergy, pollen allergy, pet dander allergy, etc.

The term "allergy," as used herein, refers to a condition caused by hypersensitivity of the immune system to a substance (allergen) in the environment. Allergies include, but are not limited to allergic asthma, hay fever, atopic dermatitis, chronic urticaria, food allergy, pet dander allergy, and pollen allergy. Symptoms of allergies may include, but are not limited to urticaria (e.g., hives), angioedema, rhinitis, asthma, vomiting, sneezing, runny nose, shortness of breath, sinus inflammation, watery eyes, wheezing, bronchospasm, reduced peak expiratory flow (PEF), gastrointestinal distress, flushing, swollen lips, swollen tongue, reduced blood pressure, anaphylaxis, and organ dysfunction/failure. In one embodiment, the allergy is an anaphylactic allergy, which is a severe form of allergy that may cause death. Symptoms of anaphylaxis may include, but are not limited to rashes, throat or tongue swelling, airway swelling, shortness of breath, vomiting, lightheadedness, low blood pressure, etc.

The term "allergen," as used herein, includes any substance, chemical, particle or composition which is capable of stimulating an allergic response in a susceptible individual. Allergens may be contained within or derived from a food item such as, e.g., dairy products (e.g., cow's milk), egg, celery, sesame, wheat, soy, fish, shellfish, sugars (e.g., sugars present on meat such as alpha-galactose), peanuts, other legumes (e.g., beans, peas, soybeans, etc.), and tree nuts. Alternatively, an allergen may be contained within or derived from a non-food item such as, e.g., dust (e.g., containing dust mite), pollen, insect venom (e.g., venom of bees, wasps, mosquitos, fire ants, etc.), mold, animal fur, animal dander, wool, latex, metals (e.g., nickel), household cleaners, detergents, medication, cosmetics (e.g., perfumes, etc.), drugs (e.g., penicillin, sulfonamides, salicylate, etc.), therapeutic monoclonal antibodies (e.g., cetuximab), ragweed, grass and birch. Exemplary pollen allergens include, e.g., tree pollens such as birch pollen, cedar pollen, oak pollen, alder pollen, hornbeam pollen, aesculus pollen, willow pollen, poplar pollen, plantanus pollen, tilia pollen, olea pollen, Ashe juniper pollen, and *Alstonia scholaris* pollen.

The term "antigen-binding molecule" includes antibodies and antigen-binding fragments of antibodies, including, e.g., bispecific antibodies.

The term "antibody", as used herein, means any antigen-binding molecule or molecular complex comprising at least one complementarity determining region (CDR) that specifically binds to or interacts with a particular antigen (e.g., FcεR1α or CD3). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, and FR4. In different embodiments of the invention, the FRs of the anti-FcεR1α antibody or anti-CD3 antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences.

In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or heterodimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments of the invention, the anti-FcεR1α monospecific antibodies or anti-FcεR1α/anti-CD3 bispecific antibodies of the invention are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention also includes one-arm antibodies that bind FcεR1α. As used herein, a "one-arm antibody" means an antigen-binding molecule comprising a single antibody heavy chain and a single antibody light chain. The one-arm antibodies of the present invention may comprise any of the HCVR/LCVR or CDR amino acid sequences as set forth in Table 1.

The anti-FcεR1α or anti-FcεR1α/anti-CD3 antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-FcεR1α or anti-FcεR1α/anti-CD3 antibodies comprising variants of any of the HCVR, LCVR, and/or CDR amino acid sequences disclosed herein having one or more conservative substitutions. For example, the present invention includes anti-FcεR1α or anti-FcεR1α/anti-CD3 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Tables 1 and 3 herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference.

Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Germline Mutations

The anti-FcεR1α and/or anti-CD3 antibodies disclosed herein comprise one or more amino acid substitutions, insertions and/or deletions in the framework and/or CDR regions of the heavy chain variable domains as compared to the corresponding germline sequences from which the antibodies were derived.

The present invention also includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"), and having desired binding properties to an FcεR1α or CD3 antigen, for example, weak or no detectable binding of anti-CD3 antibodies to CD3. Several such exemplary antibodies that recognize FcεR1α are described in Table 1. Several such exemplary antibodies that recognize CD3 are described in Table 3.

Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be tested for one or more desired properties such as, improved binding specificity, weak or reduced binding affinity, improved or enhanced pharmacokinetic properties, reduced immunogenicity, etc. Antibodies and antigen-binding fragments obtained in this general manner given the guidance of the present disclosure are encompassed within the present invention.

The present invention also includes anti-FcεR1α antibodies comprising variants of any of the HCVR, LCVR, and/or CDR amino acid sequences disclosed herein having one or more conservative substitutions. For example, the present invention includes anti-CD3 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein. The antibodies and bispecific antigen-binding molecules of the present invention comprise one or more amino acid substitutions, insertions and/or deletions in the framework and/or CDR regions of the heavy and light chain variable domains as compared to the corresponding germline sequences from which the individual antigen-binding domains were derived, while maintaining or improving the desired binding to FcεR1α or CD3, for example, weak or no detectable binding of anti-CD3 antibodies to CD3 antigen. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein, i.e. the amino acid substitution maintains or improves the desired binding affinity in the case of anti-FcεR1α and/or anti-CD3 binding molecules, for example, weak to no detectable binding or anti-CD3 antibodies to CD3 antigen. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

The present invention also includes antigen-binding molecules comprising an antigen-binding domain with an HCVR and/or CDR amino acid sequence that is substantially identical to any of the HCVR and/or CDR amino acid sequences disclosed herein, while maintaining or improving the desired property to FcεR1α and/or CD3 antigen. The term "substantial identity" or "substantially identical," when referring to an amino acid sequence means that two amino acid sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.

Once obtained, antigen-binding domains that contain one or more germline mutations are tested for decreased binding affinity utilizing one or more in vitro assays. Although antibodies that recognize a particular antigen are typically screened for their purpose by testing for high (i.e. strong) binding affinity to the antigen, the antibodies of the present invention exhibit weak binding or no detectable binding. Bispecific antigen-binding molecules comprising one or more antigen-binding domains obtained in this general manner are also encompassed within the present invention and are found to be advantageous as avidity-driven allergy therapies.

Unexpected benefits, for example, improved pharmacokinetic properties and low toxicity to the patient may be realized from the methods described herein.

Binding Properties of the Antibodies

As used herein, the term "binding" in the context of the binding of an antibody, immunoglobulin, antibody-binding fragment, or Fc-containing protein to either, e.g., a predetermined antigen, such as a cell surface protein or fragment thereof, typically refers to an interaction or association between a minimum of two entities or molecular structures, such as an antibody-antigen interaction.

For instance, binding affinity typically corresponds to a $K_D$ value of about $10^{-6}$ M or less, such as about $10^{-7}$ M or less, such as about $10^{-8}$ M or less, such as about $10^{-9}$ M or less when determined by, for instance, surface plasmon resonance (SPR) technology in a BIAcore 3000 instrument using the antigen as the ligand and the antibody, Ig, antibody-binding fragment, or Fc-containing protein as the analyte (or antiligand). Cell-based binding strategies, such as fluorescent-activated cell sorting (FACS) binding assays, are also routinely used, and FACS data correlates well with other methods such as radioligand competition binding and SPR (Benedict, C A, *J Immunol Methods.* 1997, 201(2):223-31; Geuijen, C A, et al. *J Immunol Methods.* 2005, 302(1-2):68-77).

Accordingly, the antibody or antigen-binding protein of the invention binds to the predetermined antigen or cell surface molecule (receptor) having an affinity corresponding to a $K_D$ value that is at least ten-fold lower than its affinity for binding to a non-specific antigen (e.g., BSA, casein). According to the present invention, the affinity of an antibody corresponding to a $K_D$ value that is equal to or less than ten-fold lower than a non-specific antigen may be considered non-detectable binding, however such an antibody may be paired with a second antigen binding arm for the production of a bispecific antibody of the invention.

The term "$K_D$" (M) refers to the dissociation equilibrium constant of a particular antibody-antigen interaction, or the dissociation equilibrium constant of an antibody or antibody-binding fragment binding to an antigen. There is an inverse relationship between $K_D$ and binding affinity, therefore the smaller the $K_D$ value, the higher, i.e. stronger, the affinity. Thus, the terms "higher affinity" or "stronger affinity" relate to a greater ability to form an interaction and therefore a smaller $K_D$ value, and conversely the terms "lower affinity" or "weaker affinity" relate to a lesser ability to form an interaction and therefore a larger $K_D$ value. In some circumstances, a higher binding affinity (or $K_D$) of a particular molecule (e.g. antibody) to its interactive partner molecule (e.g. antigen X) compared to the binding affinity of the molecule (e.g. antibody) to another interactive partner molecule (e.g. antigen Y) may be expressed as a binding affinity ratio determined by dividing the larger $K_D$ value (lower, or weaker, affinity) by the smaller $K_D$ (higher, or stronger, affinity), for example expressed as 5-fold or 10-fold greater binding affinity, as the case may be.

The term "$k_d$" (sec-1 or 1/s) refers to the dissociation rate constant of a particular antibody-antigen interaction, or the dissociation rate constant of an antibody or antibody-binding fragment. Said value is also referred to as the $k_{off}$ value.

The term "$k_a$" (M−1×sec-1 or 1/M) refers to the association rate constant of a particular antibody-antigen interaction, or the association rate constant of an antibody or antibody-binding fragment.

The term "$K_A$" (M−1 or 1/M) refers to the association equilibrium constant of a particular antibody-antigen interaction, or the association equilibrium constant of an antibody or antibody-binding fragment. The association equilibrium constant is obtained by dividing the $k_a$ by the $k_d$.

The term "EC50" or "$EC_{50}$" refers to the half maximal effective concentration, which includes the concentration of an antibody that induces a response halfway between the baseline and maximum after a specified exposure time. The $EC_{50}$ essentially represents the concentration of an antibody where 50% of its maximal effect is observed. In certain embodiments, the $EC_{50}$ value equals the concentration of an antibody of the invention that gives half-maximal binding to cells expressing CD3 or allergy related antigen, as determined by e.g. a FACS binding assay. Thus, reduced or weaker binding is observed with an increased $EC_{50}$, or half maximal effective concentration value.

In one embodiment, decreased binding can be defined as an increased $EC_{50}$ antibody concentration which enables binding to the half-maximal amount of target cells.

In another embodiment, the $EC_{50}$ value represents the concentration of an antibody of the invention that elicits half-maximal depletion of target cells by T cell cytotoxic activity. Thus, increased cytotoxic activity (e.g. T cell-mediated basophils killing) is observed with a decreased $EC_{50}$, or half maximal effective concentration value.

Bispecific Antigen-Binding Molecules

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-FcεR1α monospecific antibodies or anti-FcεR1α/anti-CD3 bispecific antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second or additional binding specificity.

Use of the expression "anti-CD3 antibody" or "anti-FcεR1α antibody" herein is intended to include both monospecific anti-CD3 or anti-FcεR1α antibodies as well as bispecific antibodies comprising a CD3-binding arm and an FcεR1α-binding arm. Thus, the present invention includes bispecific antibodies wherein one arm of an immunoglobulin binds human CD3, and the other arm of the immunoglobulin is specific for human FcεR1α. The CD3-binding arm can comprise any of the HCVR/LCVR or CDR amino acid sequences as set forth in Table 3 herein.

In certain embodiments, the CD3-binding arm binds to human CD3 and induces human T cell activation. In certain embodiments, the CD3-binding arm binds weakly to human CD3 and induces human T cell activation. In other embodiments, the CD3-binding arm binds weakly to human CD3 and induces ablation of mast cells and/or basophils in the context of a bispecific or multispecific antibody. In other embodiments, the CD3-binding arm binds or is associated weakly with human CD3, yet the binding interaction is not detectable by in vitro assays known in the art. The FcεR1α-binding arm can comprise any of the HCVR/LCVR or CDR amino acid sequences as set forth in Table 1 herein.

According to certain exemplary embodiments, the present invention includes bispecific antigen-binding molecules that specifically bind CD3 and FcεR1α. Such molecules may be referred to herein as, e.g., "anti-CD3/anti-FcεR1α," or "anti-CD3×FcεR1α," or "anti-FcεR1α/anti-CD3," or "anti-FcεR1α×CD3," or "CD3×FcεR1α" bispecific molecules, or "FcεR1α×CD3" bispecific molecules, or other similar terminology (e.g., anti-FcεR1α× anti-CD3).

The term "FcεR1α," as used herein, refers to the human FcεR1α protein unless specified as being from a non-human species (e.g., "mouse FcεR1α," "monkey FcεR1α," etc.). The human FcεR1α protein has the amino acid sequence shown in SEQ ID NO: 63.

The aforementioned bispecific antigen-binding molecules that specifically bind CD3 and FcεR1α may comprise an anti-CD3 antigen-binding molecule which binds to CD3 with a weak binding affinity such as exhibiting a $K_D$ of greater than about 40 nM, as measured by an in vitro affinity binding assay.

As used herein, the expression "antigen-binding molecule" means a protein, polypeptide or molecular complex comprising or consisting of at least one complementarity determining region (CDR) that alone, or in combination with one or more additional CDRs and/or framework regions (FRs), specifically binds to a particular antigen. In certain embodiments, an antigen-binding molecule is an antibody or a fragment of an antibody, as those terms are defined elsewhere herein.

As used herein, the expression "bispecific antigen-binding molecule" means a protein, polypeptide or molecular complex comprising at least a first antigen-binding domain and a second antigen-binding domain. Each antigen-binding domain within the bispecific antigen-binding molecule comprises at least one CDR that alone, or in combination with one or more additional CDRs and/or FRs, specifically binds to a particular antigen. In the context of the present invention, the first antigen-binding domain specifically binds a first antigen (e.g., CD3), and the second antigen-binding domain specifically binds a second, distinct antigen (e.g., FcεR1α).

In certain exemplary embodiments of the present invention, the bispecific antigen-binding molecule is a bispecific antibody. Each antigen-binding domain of a bispecific antibody comprises a heavy chain variable domain (HCVR) and a light chain variable domain (LCVR). In the context of a bispecific antigen-binding molecule comprising a first and a second antigen-binding domain (e.g., a bispecific antibody), the CDRs of the first antigen-binding domain may be designated with the prefix "A1" and the CDRs of the second antigen-binding domain may be designated with the prefix "A2". Thus, the CDRs of the first antigen-binding domain may be referred to herein as A1-HCDR1, A1-HCDR2, and A1-HCDR3; and the CDRs of the second antigen-binding domain may be referred to herein as A2-HCDR1, A2-HCDR2, and A2-HCDR3.

The first antigen-binding domain and the second antigen-binding domain may be directly or indirectly connected to one another to form a bispecific antigen-binding molecule of the present invention. Alternatively, the first antigen-binding domain and the second antigen-binding domain may each be connected to a separate multimerizing domain. The association of one multimerizing domain with another multimerizing domain facilitates the association between the two antigen-binding domains, thereby forming a bispecific antigen-binding molecule. As used herein, a "multimerizing domain" is any macromolecule, protein, polypeptide, peptide, or amino acid that has the ability to associate with a second multimerizing domain of the same or similar structure or constitution. For example, a multimerizing domain may be a polypeptide comprising an immunoglobulin $C_H3$ domain. A non-limiting example of a multimerizing component is an Fc portion of an immunoglobulin (comprising a $C_H2$-$C_H3$ domain), e.g., an Fc domain of an IgG selected from the isotypes IgG1, IgG2, IgG3, and IgG4, as well as any allotype within each isotype group.

Bispecific antigen-binding molecules of the present invention will typically comprise two multimerizing domains, e.g., two Fc domains that are each individually part of a separate antibody heavy chain. The first and second multimerizing domains may be of the same IgG isotype such as, e.g., IgG1/IgG1, IgG2/IgG2, and IgG4/IgG4. Alternatively, the first and second multimerizing domains may be of different IgG isotypes such as, e.g., IgG1/IgG2, IgG1/IgG4, IgG2/IgG4, etc.

In certain embodiments, the multimerizing domain is an Fc fragment or an amino acid sequence of from 1 to about 200 amino acids in length containing at least one cysteine residue. In other embodiments, the multimerizing domain is a cysteine residue, or a short cysteine-containing peptide. Other multimerizing domains include peptides or polypeptides comprising or consisting of a leucine zipper, a helix-loop motif, or a coiled-coil motif.

Any bispecific antibody format or technology may be used to make the bispecific antigen-binding molecules of the present invention. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats).

In the context of bispecific antigen-binding molecules of the present invention, the multimerizing domains, e.g., Fc domains, may comprise one or more amino acid changes (e.g., insertions, deletions or substitutions) as compared to the wild-type, naturally occurring version of the Fc domain. For example, the invention includes bispecific antigen-binding molecules comprising one or more modifications in the Fc domain that results in a modified Fc domain having a modified binding interaction (e.g., enhanced or diminished) between Fc and FcRn. In one embodiment, the bispecific antigen-binding molecule comprises a modification in a $C_H2$ or a $C_H3$ region, wherein the modification increases the affinity of the Fc domain to FcRn in an acidic environment (e.g., in an endosome where pH ranges from about 5.5 to about 6.0). Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., F or P), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

The present invention also includes bispecific antigen-binding molecules comprising a first $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). See, for example, U.S. Pat. No. 8,586,713. Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies.

In certain embodiments, the Fc domain may be chimeric, combining Fc sequences derived from more than one immunoglobulin isotype. For example, a chimeric Fc domain can comprise part or all of a $C_H2$ sequence derived from a human IgG1, human IgG2 or human IgG4 $C_H2$ region, and part or all of a $C_H3$ sequence derived from a human IgG1, human IgG2 or human IgG4. A chimeric Fc domain can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric Fc domain that can be included in any of the antigen-binding molecules set forth herein comprises, from N- to C-terminus: [IgG4 $C_H1$]-[IgG4 upper hinge]-[IgG2 lower hinge]-[IgG4 CH2]-[IgG4 CH3]. Another example of a chimeric Fc domain that can be included in any of the antigen-binding molecules set forth herein comprises, from N- to C-terminus: [IgG1 $C_H1$]-[IgG1 upper hinge]-[IgG2 lower hinge]-[IgG4 CH2]-[IgG1 CH3]. These and other examples of chimeric Fc domains that can be included in any of the antigen-binding molecules of the present invention are described in US Publication 2014/0243504, published Aug. 28, 2014, which is herein incorporated in its entirety. Chimeric Fc domains having these general structural arrangements, and variants thereof, can have altered Fc receptor binding, which in turn affects Fc effector function.

In certain embodiments, the invention provides an antibody heavy chain wherein the heavy chain constant region (CH) region comprises an amino acid sequence at least 95%, at least 96%, at least 97%, at least 98%, at least 99% identical to any one of SEQ ID NO: 34, SEQ ID NO: 36, SEQ ID NO: 38, or SEQ ID NO: 56. In some embodiments, the heavy chain constant region (CH) region comprises an amino acid sequence selected from the group consisting of SEQ ID NO: 34, SEQ ID NO: 36, SEQ ID NO: 38, and SEQ ID NO: 56.

Sequence Variants

The antibodies and bispecific antigen-binding molecules of the present invention may comprise one or more amino acid substitutions, insertions and/or deletions in the framework and/or CDR regions of the heavy and light chain variable domains as compared to the corresponding germline sequences from which the individual antigen-binding domains were derived. Such mutations can be readily ascertained by comparing the amino acid sequences disclosed herein to germline sequences available from, for example, public antibody sequence databases. The antigen-binding molecules of the present invention may comprise antigen-binding domains which are derived from any of the exemplary amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antigen-binding domain was originally derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antigen-binding domain was originally derived). Furthermore, the antigen-binding domains may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antigen-binding domains that contain one or more germline mutations can be easily tested for one or more desired property such as, improved binding specificity, increased binding affinity, improved or enhanced antagonistic or agonistic biological properties (as the case may be), reduced immunogenicity, etc. Bispecific antigen-binding molecules comprising one or more antigen-binding domains obtained in this general manner are encompassed within the present invention.

The present invention also includes antigen-binding molecules wherein one or both antigen-binding domains comprise variants of any of the HCVR, LCVR, and/or CDR amino acid sequences disclosed herein having one or more conservative substitutions. For example, the present invention includes antigen-binding molecules comprising an antigen-binding domain having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al.

(1992) Science 256: 1443-1445, herein incorporated by reference. A "moderately conservative" replacement is any change having a nonnegative value in the PAM250 log-likelihood matrix.

The present invention also includes antigen-binding molecules comprising an antigen-binding domain with an HCVR, LCVR, and/or CDR amino acid sequence that is substantially identical to any of the HCVR, LCVR, and/or CDR amino acid sequences disclosed herein. The term "substantial identity" or "substantially identical," when referring to an amino acid sequence means that two amino acid sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

pH-Dependent Binding

The present invention includes anti-FcεR1α antibodies, and anti-CD3/anti-FcεR1α bispecific antigen-binding molecules, with pH-dependent binding characteristics. For example, an anti-FcεR1α antibody of the present invention may exhibit reduced binding to FcεR1α at acidic pH as compared to neutral pH. Alternatively, anti-FcεR1α antibodies of the invention may exhibit enhanced binding to FcεR1α at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding . . . at acidic pH as compared to neutral pH" is expressed in terms of a ratio of the $K_D$ value of the antibody binding to its antigen at acidic pH to the $K_D$ value of the antibody binding to its antigen at neutral pH (or vice versa). For example, an antibody or antigen-binding fragment thereof may be regarded as exhibiting "reduced binding to FcεR1α at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Antibodies Comprising Fc Variants

According to certain embodiments of the present invention, anti-FcεR1α antibodies, and anti-CD3/anti-FcεR1α bispecific antigen-binding molecules, are provided comprising an Fc domain comprising one or more mutations which enhance or diminish antibody binding to the FcRn receptor, e.g., at acidic pH as compared to neutral pH. For example, the present invention includes antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 and/or 308 (e.g., F or P), and 434. In one embodiment, the modification comprises a 428L (e.g., M428L) and 434S (e.g., N434S) modification; a 428L, 2591 (e.g., V2591), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); a 307 modification and/or a 308 modification (e.g., 308F or 308P).

For example, the present invention includes anti-FcεR1α antibodies, and anti-CD3/anti-FcεR1α bispecific antigen-binding molecules, comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Biological Characteristics of the Antibodies and Bispecific Antigen-Binding Molecules According to certain embodiments, the present invention includes antibodies and antigen-binding fragments of antibodies that bind human FcεR1α (e.g., at 25° C.) with a $K_D$ of less than about 303 nM or bind cynomolgus FcεR1α (e.g., at 25° C.) with a $K_D$ of less than about 467 nM as measured by surface plasmon resonance, e.g., using an assay format as defined in Example 3 herein. In certain embodiments, the antibodies or antigen-binding fragments of the present invention bind human or cynomolgus FcεR1α with a $K_D$ of less than about 400 nM, less than about 500 nM, less than about 450 nM, less than about 400 nM, less than about 350 nM, less than about 300 nM, less than about 250 nM, less than about 200 nM, less than about 150 nM, or less than about 100 nM, as measured by surface plasmon resonance, e.g., using an assay format as defined in Example 3 herein (e.g., mAb-capture or antigen-capture format), or a substantially similar assay.

The present invention includes bispecific antigen-binding molecules (e.g., bispecific antibodies which bind human or cynomolgus FcεR1α with a $K_D$ of less than about 467 nM, as measured by surface plasmon resonance, e.g., using an assay format as defined in Example 3 herein (e.g., mAb-capture or antigen-capture format), or a substantially similar assay.

The present invention also includes antibodies and antigen-binding fragments thereof that bind human FcεR1α with a dissociative half-life (t½) of greater than about 0.2 minute or greater than about 0.5 minutes or bind cynomolgus FcεR1α with a dissociative half-life (t½) of greater than about 0.3 minute or greater than about 0.6 minute as measured by surface plasmon resonance at 25° C., e.g., using an assay format as defined in Example 3 herein, or a substantially similar assay. The present invention includes bispecific antigen-binding molecules (e.g., bispecific antibodies) which bind human or cynomolgus FcεR1α with a $K_D$ of greater than about 0.54 minutes or greater than about 1.1 minutes as measured by surface plasmon resonance at 25° C., e.g., using an assay format as defined in Example 3 herein, or a substantially similar assay.

The present invention also includes antibodies and antigen-binding fragments thereof which bind specifically to human cell lines which express human or cynomolgus FcεR1α (e.g., HEK293 cells engineered to express human or cynomolgus FcεR1α), as determined by a flow cytometry-based detection assay as set forth in Example 4 or a substantially similar assay.

The present invention also includes anti-CD3/anti-FcεR1α bispecific antigen-binding molecules which exhibit one or more characteristics selected from the group consisting of: (a) binding to FcεR1α expressed on cell surface in the absence or presence of IgE (see, e.g., Example 4); (b) activating human CD3 signaling in the presence of FcεR1α expressing cells (see, e.g., Example 5); (c) inducing T-cell mediated apoptosis of FcεR1α expressing cells in vitro (see, e.g., Example 6); (d) inducing T-cell mediated killing of basophils in a peripheral blood mononuclear cell (PBMC) population in vitro (see, e.g., Example 6); (e) blocking allergen induced mast cell degranulation (e.g., anaphylaxis) in mice expressing human FcεR1α (see, e.g., Example 7); and (f) depleting splenic basophils in mice expressing human FcεR1α (see, e.g., Example 7).

The present invention includes antibodies and antigen-binding fragments thereof that bind human CD3 with high affinity. The present invention also includes antibodies and antigen-binding fragments thereof that bind human CD3 with medium or low affinity, depending on the therapeutic context and particular targeting properties that are desired. The present invention also includes antibodies and antigen-binding fragments thereof that bind human CD3 with no measureable affinity. For example, in the context of a bispecific antigen-binding molecule, wherein one arm binds CD3 and another arm binds a target antigen (e.g., FcεR1α), it may be desirable for the target antigen-binding arm to bind the target antigen with high affinity while the anti-CD3 arm binds CD3 with only moderate or low affinity or no affinity. In this manner, preferential targeting of the antigen-binding molecule to cells expressing the target antigen may be achieved while avoiding general/untargeted CD3 binding and the consequent adverse side effects associated therewith.

The present invention includes bispecific antigen-binding molecules (e.g., bispecific antibodies) which are capable of simultaneously binding to human CD3 and a human FcεR1α. The binding arm that interacts with cells that express CD3 may have weak to no detectable binding as measured in a suitable in vitro binding assay. The extent to which a bispecific antigen-binding molecule binds cells that express CD3 and/or FcεR1α can be assessed by fluorescence activated cell sorting (FACS), as illustrated in Example 4 herein.

For example, the present invention includes antibodies, antigen-binding fragments, and bispecific antibodies thereof which specifically bind human T-cell lines which express CD3 but do not express FcεR1α, primate T-cells (e.g., cynomolgus peripheral blood mononuclear cells [PBMCs]), and/or FcεR1α-expressing cells.

The present invention includes antibodies, antigen-binding fragments, and bispecific antibodies thereof that bind human CD3 with weak (i.e. low) or even no detectable affinity.

The present invention includes antibodies, antigen-binding fragments, and bispecific antibodies thereof that bind monkey (cynomolgus) CD3 with weak (i.e. low) or even no detectable affinity.

The present invention includes antibodies, antigen-binding fragments, and bispecific antibodies thereof that bind human CD3 and induce T cell activation.

The present invention includes anti-CD3/anti-FcεR1α bispecific antigen-binding molecules which are capable of inhibiting allergic response and/or depleting FcεR1α-expressing cells in a subject (see, e.g., Example 7, in a passive cutaneous anaphylaxis (PCA) or a flow cytometry-based assay, or substantially similar assays). For example, according to certain embodiments, anti-CD3/anti-FcεR1α bispecific antigen-binding molecules are provided, wherein a single administration of 25 mg/kg of the bispecific antigen-binding molecule to a subject causes a reduction in the number of FcεR1α-expressing cells in the subject (e.g., the number of splenic basophils is significantly reduced).

Epitope Mapping and Related Technologies

The epitope on CD3 and/or FcεR1α to which the antigen-binding molecules of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a CD3 or FcεR1α protein. Alternatively, the epitope may consist of a plurality of non-contiguous amino acids (or amino acid sequences) of CD3 or FcεR1α. The antibodies of the invention may interact with amino acids contained within a single CD3 chain (e.g., CD3-epsilon, CD3-delta or CD3-gamma), or may interact with amino acids on two or more different CD3 chains. The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstances, an epitope may include moieties of saccharides, phosphoryl groups, or sulfonyl groups on the antigen.

Various techniques known to persons of ordinary skill in the art can be used to determine whether an antigen-binding domain of an antibody "interacts with one or more amino acids" within a polypeptide or protein. Exemplary techniques include, e.g., routine cross-blocking assay such as that described Antibodies, Harlow and Lane (Cold Spring Harbor Press, Cold Spring Harbor, N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antigen-binding domain of an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267(2):252-259; Engen and Smith (2001) Anal. Chem. 73:256A-265A. X-ray crystallography of the antigen/antibody complex may also be used for epitope mapping purposes.

The present invention further includes anti-FcεR1α antibodies that bind to the same epitope as any of the specific exemplary antibodies described herein (e.g. antibodies comprising any of the amino acid sequences as set forth in Table 1 herein). Likewise, the present invention also includes anti-FcεR1α antibodies that compete for binding to FcεR1α with any of the specific exemplary antibodies described herein (e.g. antibodies comprising any of the amino acid sequences as set forth in Table 1 herein).

The present invention also includes bispecific antigen-binding molecules comprising a first antigen-binding domain that specifically binds human CD3 and/or cynomolgus CD3 with low or detectable binding affinity, and a second antigen binding domain that specifically binds human or cynomolgus FcεR1α, wherein the first antigen-binding domain binds to the same epitope on CD3 as any of the specific exemplary CD3-specific antigen-binding domains described herein, and/or wherein the second antigen-binding domain binds to the same epitope on FcεR1α as any of the specific exemplary FcεR1α-specific antigen-binding domains described herein.

Likewise, the present invention also includes bispecific antigen-binding molecules comprising a first antigen-binding domain that specifically binds human CD3, and a second antigen binding domain that specifically binds human FcεR1α, wherein the first antigen-binding domain competes for binding to CD3 with any of the specific exemplary CD3-specific antigen-binding domains described herein, and/or wherein the second antigen-binding domain competes for binding to FcεR1α with any of the specific exemplary FcεR1α-specific antigen-binding domains described herein.

One can easily determine whether a particular antigen-binding molecule (e.g., antibody) or antigen-binding domain thereof binds to the same epitope as, or competes for binding with, a reference antigen-binding molecule of the present invention by using routine methods known in the art. For example, to determine if a test antibody binds to the same epitope on FcεR1α (or CD3) as a reference bispecific antigen-binding molecule of the present invention, the reference bispecific molecule is first allowed to bind to an FcεR1α protein (or CD3 protein). Next, the ability of a test antibody to bind to the FcεR1α (or CD3) molecule is assessed. If the test antibody is able to bind to FcεR1α (or CD3) following saturation binding with the reference bispecific antigen-binding molecule, it can be concluded that the test antibody binds to a different epitope of FcεR1α (or CD3) than the reference bispecific antigen-binding molecule. On the other hand, if the test antibody is not able to bind to the FcεR1α (or CD3) molecule following saturation binding with the reference bispecific antigen-binding molecule, then the test antibody may bind to the same epitope of FcεR1α (or CD3) as the epitope bound by the reference bispecific antigen-binding molecule of the invention. Additional routine experimentation (e.g., peptide mutation and binding analyses) can then be carried out to confirm whether the observed lack of binding of the test antibody is in fact due to binding to the same epitope as the reference bispecific antigen-binding molecule or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antigen-binding proteins bind to the same (or overlapping) epitope if, e.g., a 1-, 5-, 10-, 20- or 100-fold excess of one antigen-binding protein inhibits binding of the other by at least 50% but preferably 75%, 90% or even 99% as measured in a competitive binding assay (see, e.g., Junghans et al., Cancer Res. 1990:50:1495-1502). Alternatively, two antigen-binding proteins are deemed to bind to the same epitope if essentially all amino acid mutations in the antigen that reduce or eliminate binding of one antigen-binding protein reduce or eliminate binding of the other. Two antigen-binding proteins are deemed to have "overlapping epitopes" if only a subset of the amino acid mutations that reduce or eliminate binding of one antigen-binding protein reduce or eliminate binding of the other.

To determine if an antibody or antigen-binding domain thereof competes for binding with a reference antigen-binding molecule, the above-described binding methodology is performed in two orientations: In a first orientation, the reference antigen-binding molecule is allowed to bind to an FcεR1α protein (or CD3 protein) under saturating conditions followed by assessment of binding of the test antibody to the FcεR1α (or CD3) molecule. In a second orientation, the test antibody is allowed to bind to an FcεR1α (or CD3) molecule under saturating conditions followed by assessment of binding of the reference antigen-binding molecule to the FcεR1α (or CD3) molecule. If, in both orientations, only the first (saturating) antigen-binding molecule is capable of binding to the FcεR1α (or CD3) molecule, then it is concluded that the test antibody and the reference antigen-binding molecule compete for binding to FcεR1α (or CD3). As will be appreciated by a person of ordinary skill in the art, an antibody that competes for binding with a reference antigen-binding molecule may not necessarily bind to the same epitope as the reference antibody, but may sterically block binding of the reference antibody by binding an overlapping or adjacent epitope.

Preparation of Antigen-Binding Domains and Construction of Bispecific Molecules

Antigen-binding domains specific for particular antigens can be prepared by any antibody generating technology known in the art. Once obtained, two different antigen-binding domains, specific for two different antigens (e.g., CD3 and FcεR1α), can be appropriately arranged relative to one another to produce a bispecific antigen-binding molecule of the present invention using routine methods. (A discussion of exemplary bispecific antibody formats that can be used to construct the bispecific antigen-binding molecules of the present invention is provided elsewhere herein). In certain embodiments, one or more of the individual components (e.g., heavy and light chains) of the multispecific antigen-binding molecules of the invention are derived from chimeric, humanized or fully human antibodies. Methods for making such antibodies are well known in the art. For example, one or more of the heavy and/or light chains of the bispecific antigen-binding molecules of the present invention can be prepared using VELOCIMMUNE™ technology. Using VELOCIMMUNE™ technology (or any other human antibody generating technology), high affinity chimeric antibodies to a particular antigen (e.g., CD3 or FcεR1α) are initially isolated having a human variable region and a mouse constant region. The antibodies are characterized and selected for desirable characteristics, including affinity, selectivity, epitope, etc. The mouse constant regions are replaced with a desired human constant region to generate fully human heavy and/or light chains that can be incorporated into the bispecific antigen-binding molecules of the present invention.

Genetically engineered animals may be used to make human bispecific antigen-binding molecules. For example, a genetically modified mouse can be used which is incapable of rearranging and expressing an endogenous mouse immunoglobulin light chain variable sequence, wherein the mouse expresses only one or two human light chain variable domains encoded by human immunoglobulin sequences operably linked to the mouse kappa constant gene at the endogenous mouse kappa locus. Such genetically modified mice can be used to produce fully human bispecific antigen-binding molecules comprising two different heavy chains that associate with an identical light chain that comprises a variable domain derived from one of two different human light chain variable region gene segments. (See, e.g., US 2011/0195454). Fully human refers to an antibody, or antigen-binding fragment or immunoglobulin domain thereof, comprising an amino acid sequence encoded by a DNA derived from a human sequence over the entire length of each polypeptide of the antibody or antigen-binding fragment or immunoglobulin domain thereof. In some instances, the fully human sequence is derived from a protein endogenous to a human. In other instances, the fully human protein or protein sequence comprises a chimeric sequence wherein each component sequence is derived from human sequence. While not being bound by any one theory, chimeric proteins or chimeric sequences are generally designed to minimize the creation of immunogenic epitopes in the junctions of component sequences, e.g. compared to any wild-type human immunoglobulin regions or domains.

Bioequivalents

The present invention encompasses antigen-binding molecules having amino acid sequences that vary from those of the exemplary molecules disclosed herein but that retain the ability to bind CD3 and/or FcεR1α. Such variant molecules may comprise one or more additions, deletions, or substitutions of amino acids when compared to parent sequence, but exhibit biological activity that is essentially equivalent to that of the described bispecific antigen-binding molecules.

The present invention includes antigen-binding molecules that are bioequivalent to any of the exemplary antigen-binding molecules set forth herein. Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antigen-binding proteins will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antigen-binding protein.

Bioequivalent variants of the exemplary bispecific antigen-binding molecules set forth herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antigen-binding proteins may include variants of the exemplary bispecific antigen-binding molecules set forth herein comprising amino acid changes which modify the glycosylation characteristics of the molecules, e.g., mutations which eliminate or remove glycosylation.

Species Selectivity and Species Cross-Reactivity

According to certain embodiments of the invention, antigen-binding molecules are provided which bind to human CD3. Also provided are antigen-binding molecules which bind to human FcεR1α. The present invention also includes antigen-binding molecules that bind to human CD3 to CD3 from one or more non-human species; and/or antigen-binding molecules that bind to human FcεR1α or and to FcεR1α from one or more non-human species, e.g., cynomolgus.

According to certain exemplary embodiments of the invention, antigen-binding molecules are provided which bind to human CD3 and/or human FcεR1α and may bind or not bind, as the case may be, to one or more of mouse, rat, guinea pig, hamster, gerbil, pig, cat, dog, rabbit, goat, sheep, cow, horse, camel, cynomolgus, marmoset, rhesus, cynomolgus or chimpanzee CD3 and/or FcεR1α. For example, in a particular exemplary embodiment of the present invention bispecific antigen-binding molecules are provided comprising a first antigen-binding domain that binds human CD3, and a second antigen-binding domain that binds human or cynomolgus FcεR1α.

Therapeutic Formulation and Administration

The present invention provides pharmaceutical compositions comprising the antigen-binding molecules of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antigen-binding molecule administered to a patient may vary depending upon the age and the size of the patient, target disease, conditions, route of administration, and the like.

The preferred dose is typically calculated according to body weight or body surface area. When a bispecific antigen-binding molecule of the present invention is used for therapeutic purposes in an adult patient, it may be advantageous to intravenously administer the bispecific antigen-binding molecule of the present invention normally at a single dose of about 0.01 to about 50 mg/kg body weight, more preferably about 0.1 to about 25, about 1 to about 25, or about 5 to about 25 mg/kg body weight. Depending on the severity of the condition, the frequency and the duration of the treatment can be adjusted. Effective dosages and schedules for administering a bispecific antigen-binding molecule may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antigen-Binding Molecules

The present invention includes methods comprising administering to a subject in need thereof a therapeutic composition comprising an anti-FcεR1α antibody or antigen-binding fragment thereof, or a bispecific antigen-binding molecule that specifically binds CD3 and FcεR1α. The therapeutic composition can comprise any of the antibodies or bispecific antigen-binding molecules as disclosed herein and a pharmaceutically acceptable carrier or diluent. As used herein, the expression "a subject in need thereof" means a human or non-human animal that exhibits one or more symptoms or indicia of an FcεR1α-related disease or disorder such as mast cell activation disorder, mastocytosis or an allergy (e.g., a subject suffering from any type of allergies or exhibiting any allergic response), or who otherwise would benefit from an inhibition or reduction in FcεR1α activity or a depletion of FcεR1α+ cells (e.g., anaphylaxis).

The antibodies and bispecific antigen-binding molecules of the invention (and therapeutic compositions comprising the same) are useful, inter alia, for treating any disease or disorder in which stimulation, activation and/or targeting of an immune response would be beneficial. In particular, the anti-FcεR1α antibodies or the anti-CD3/anti-FcεR1α bispecific antigen-binding molecules of the present invention may be used for the treatment, prevention and/or amelioration of any disease or disorder associated with or mediated by FcεR1α expression or activity or the proliferation of FcεR1α+ cells. The mechanism of action by which the therapeutic methods of the invention are achieved include killing of the cells expressing FcεR1α in the presence of effector cells, for example, by CDC, apoptosis, ADCC, phagocytosis, or by a combination of two or more of these mechanisms. Cells expressing FcεR1α which can be inhibited or killed using the bispecific antigen-binding molecules of the invention include, for example, mast cells and/or basophils.

The antigen-binding molecules of the present invention may be used to treat a disease or disorder associated with IgE or FcεR1α expression including, e.g., mast cell activation disorder (such as mast cell activation syndrome), mastocytosis, or allergies including allergic asthma, hay fever, anaphylaxis, atopic dermatitis, chronic urticaria, food allergy, and pollen allergy. The allergies may be caused by exposure to one or more allergens, as listed elsewhere herein. According to certain embodiments of the present invention, the anti-FcεR1α antibodies or anti-FcεR1α/anti-CD3 bispecific antibodies are useful for treating a patient afflicted with severe allergy, including anaphylaxis. According to other related embodiments of the invention, methods are provided comprising administering an anti-FcεR1α antibody or an anti-CD3/anti-FcεR1α bispecific antigen-binding molecule as disclosed herein to a patient who is afflicted with anaphylaxis. Analytic/diagnostic methods known in the art, such as allergic reaction test, etc., may be used to ascertain whether a patient suffers anaphylaxis.

According to certain aspects, the present invention provides methods for treating a disease or disorder associated with FcεR1α expression (e.g., anaphylaxis) comprising administering one or more of the anti-FcεR1α or bispecific antigen-binding molecules described elsewhere herein to a subject after the subject has been determined to have allergy. For example, the present invention includes methods for treating allergy comprising administering an anti-FcεR1α antibody or an anti-CD3/anti-FcεR1α bispecific antigen-binding molecule to a patient 1 day, 2 days, 3 days, 4 days, 5 days, 6 days, 1 week, 2 weeks, 3 weeks or 4 weeks, 2 months, 4 months, 6 months, 8 months, 1 year, or more after the subject has received other therapy (e.g., anti-histamine therapy).

Combination Therapies and Formulations

The present invention provides methods which comprise administering a pharmaceutical composition comprising any of the exemplary antibodies and bispecific antigen-binding molecules described herein in combination with one or more additional therapeutic agents.

Exemplary additional therapeutic agents that may be combined with or administered in combination with an antigen-binding molecule of the present invention include, e.g., an IgE antagonist (e.g., an anti-IgE antibody such as omalizumab) or small molecule inhibitor of IgE (e.g., darpins such as darpin E2_76), an IL-25 inhibitor, an IL-4 inhibitor, an IL-4 receptor inhibitor (e.g., an anti-IL-4R antibody such as dupilumab), an IL-33 inhibitor (e.g., an anti-IL-33 antibody), a plasma cell ablating agent (e.g., a BCMA×CD3 bispecific antibody) and a TSLP inhibitor. In certain embodiments, the plasma cell ablating agent is selected from the group consisting of a B-cell maturation antigen (BCMA) targeting agent, a proteasome inhibitor, a histone deacetylase inhibitor, a B-cell activating factor (BAFF) inhibitor, and an inhibitor of A proliferation inducing ligand (APRIL; CD256). In one embodiment, the BCMA targeting agent is selected from the group consisting of an anti-BCMA/anti-CD3 bispecific antibody, a chimeric antigen receptor against BCMA, and an anti-BCMA antibody conjugated to a cytotoxic drug.

Other agents that may be beneficially administered in combination with the antigen-binding molecules of the invention include allergy treatment medicines, including antihistamines, anti-inflammatory agents, corticoids, epinephrine, a bronchial dilator, a decongestant, leukotriene antagonists, or mast cell inhibitor (e.g., cromolyn sodium).

The present invention also includes therapeutic combinations comprising any of the antigen-binding molecules mentioned herein and an inhibitor of IgE or FcεR1α, wherein the inhibitor is an aptamer, an antisense molecule, a ribozyme, an siRNA, a peptibody, a nanobody or an antibody fragment (e.g., Fab fragment; F(ab')$_2$ fragment; Fd fragment; Fv fragment; scFv; dAb fragment; or other engineered molecules, such as diabodies, triabodies, tetrabodies, minibodies and minimal recognition units). The antigen-binding molecules of the invention may also be administered and/or co-formulated in combination with antivirals, antibiotics, analgesics, corticosteroids and/or NSAIDs.

The additional therapeutically active component(s) may be administered just prior to, concurrent with, or shortly after the administration of an antigen-binding molecule of the present invention; (for purposes of the present disclosure, such administration regimens are considered the administration of an antigen-binding molecule "in combination with" an additional therapeutically active component).

The present invention includes pharmaceutical compositions in which an antigen-binding molecule of the present invention is co-formulated with one or more of the additional therapeutically active component(s) as described elsewhere herein.

Administration Regimens

According to certain embodiments of the present invention, multiple doses of an antigen-binding molecule (e.g., an anti-FcεR1α antibody or a bispecific antigen-binding molecule that specifically binds FcεR1α and CD3) may be administered to a subject over a defined time course. The methods according to this aspect of the invention comprise sequentially administering to a subject in need thereof multiple doses of an antigen-binding molecule of the invention. As used herein, "sequentially administering" means that each dose of an antigen-binding molecule is administered to the subject at a different point in time, e.g., on different days separated by a predetermined interval (e.g., hours, days, weeks or months). The present invention includes methods which comprise sequentially administering to the patient a single initial dose of an antigen-binding molecule, followed by one or more secondary doses of the antigen-binding molecule, and optionally followed by one or more tertiary doses of the antigen-binding molecule.

The terms "initial dose," "secondary doses," and "tertiary doses," refer to the temporal sequence of administration of the antigen-binding molecule of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the antigen-binding molecule, but generally may differ from one another in terms of frequency of administration. In certain embodiments, however, the amount of an antigen-binding molecule contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of antigen-binding molecule which is administered to a patient prior to the administration of the very next dose in the sequence with no intervening doses.

The methods according to this aspect of the invention may comprise administering to a patient any number of secondary and/or tertiary doses of an antigen-binding molecule (e.g., an anti-FcεR1α antibody or a bispecific antigen-binding molecule that specifically binds FcεR1α and CD3). For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

In one embodiment, the antigen-binding molecule (e.g., an anti-FcεR1α antibody or a bispecific antigen-binding molecule that specifically binds FcεR1α and CD3) is administered to a subject as a weight-based dose. A "weight-based dose" (e.g., a dose in mg/kg) is a dose of the antibody or the antigen-binding fragment thereof or the bispecific antigen-binding molecule that will change depending on the subject's weight.

In another embodiment, an antibody or the antigen-binding fragment thereof or a bispecific antigen-binding molecule is administered to a subject as a fixed dose. A "fixed dose" (e.g., a dose in mg) means that one dose of the antibody or the antigen-binding fragment thereof or the bispecific antigen-binding molecule is used for all subjects regardless of any specific subject-related factors, such as weight. In one particular embodiment, a fixed dose of an antibody or the antigen-binding fragment thereof or a bispecific antigen-binding molecule of the invention is based on a predetermined weight or age.

In general, a suitable dose of the antigen binding molecule the invention can be in the range of about 0.001 to about 200.0 milligram per kilogram body weight of the recipient, generally in the range of about 1 to 50 mg per kilogram body weight. For example, the antibody or the antigen-binding fragment thereof or the bispecific antigen-binding molecule can be administered at about 0.1 mg/kg, about 0.5 mg/kg, about 1 mg/kg, about 1.5 mg/kg, about 2 mg/kg, about 3 mg/kg, about 5 mg/kg, about 10 mg/kg, about 15 mg/kg, about 20 mg/kg, about 25 mg/kg, about 30 mg/kg, about 40 mg/kg, about 50 mg/kg per single dose. Values and ranges intermediate to the recited values are also intended to be part of this invention.

In some embodiments, the antigen binding molecule of the invention is administered as a fixed dose of between about 1 mg to about 2500 mg. In some embodiments, the antigen binding molecule of the invention is administered as a fixed dose of about 1 mg, 2 mg, 3 mg, 5 mg, 10 mg, 15 mg, 20 mg, 25 mg, about 30 mg, about 50 mg, about 75 mg, about 100 mg, about 125 mg, about 150 mg, about 175 mg, 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1500 mg, about 2000 mg, or about 2500 mg. Values and ranges intermediate to the recited values are also intended to be part of this invention.

Diagnostic Uses of the Antibodies

The anti-FcεR1α antibodies of the present invention may also be used to detect and/or measure FcεR1α, or FcεR1α-expressing cells in a sample, e.g., for diagnostic purposes. For example, an anti-FcεR1α antibody, or fragment thereof, may be used to diagnose a condition or disease characterized by aberrant expression (e.g., over-expression, under-expression, lack of expression, etc.) of FcεR1α. Exemplary diagnostic assays for FcεR1α may comprise, e.g., contacting a sample, obtained from a patient, with an anti-FcεR1α antibody of the invention, wherein the anti-FcεR1α antibody is labeled with a detectable label or reporter molecule. Alternatively, an unlabeled anti-FcεR1α antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Another exemplary diagnostic use of the anti-FcεR1α antibodies of the invention includes $^{89}$Zr-labeled, such as $^{89}$Zr-desferrioxamine-labeled, antibody for the purpose of noninvasive identification and tracking of mast cells, basophils, or other FcεR1α expressing cells in a subject (e.g. positron emission tomography (PET) imaging). (See, e.g., Tavare, R. et al. Cancer Res. 2016 Jan. 1; 76(1):73-82; and Azad, B B. et al. Oncotarget. 2016 Mar. 15; 7(11):12344-58.) Specific exemplary assays that can be used to detect or measure FcεR1α in a sample include enzyme-linked immunosorbent assay (ELISA), radioimmunoassay (RIA), and fluorescence-activated cell sorting (FACS).

Samples that can be used in FcεR1α diagnostic assays according to the present invention include any tissue or fluid sample obtainable from a patient which contains detectable quantities of FcεR1α protein, or fragments thereof, under normal or pathological conditions. Generally, levels of FcεR1α in a particular sample obtained from a healthy patient (e.g., a patient not afflicted with a disease or condition associated with abnormal FcεR1α levels or activity) will be measured to initially establish a baseline, or standard, level of FcεR1α. This baseline level of FcεR1α can then be compared against the levels of FcεR1α measured in samples obtained from individuals suspected of having an FcεR1α related disease (e.g., a subject with allergy) or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Generation of Antibodies

Generation of Anti-FcεR1α Antibodies

Anti-FcεR1α antibodies were obtained by immunizing a genetically modified mouse with a human FcεR1α antigen (e.g., hFcεR1α, SEQ ID NO: 63) or by immunizing an engineered mouse comprising DNA encoding human immunoglobulin heavy and kappa light chain variable regions with a human FcεR1α antigen.

Following immunization, splenocytes were harvested from each mouse and either (1) fused with mouse myeloma cells to preserve their viability and form hybridoma cells and screened for FcεR1α specificity, or (2) B-cell sorted (as described in US 2007/0280945A1) using a human FcεR1α fragment as the sorting reagent that binds and identifies reactive antibodies (antigen-positive B cells).

Chimeric antibodies to FcεR1α were initially isolated having a human variable region and a mouse constant region. The antibodies were characterized and selected for desirable characteristics, including affinity, selectivity, etc. If necessary, mouse constant regions were replaced with a desired human constant region, for example wild-type or modified IgG1 or IgG4 constant region, to generate a fully human anti-FcεR1α antibody. While the constant region selected may vary according to specific use, high affinity antigen-binding and target specificity characteristics reside in the variable region.

Certain biological properties of the exemplary anti-FcεR1α antibodies generated in accordance with the methods of this Example are described in detail in the Examples set forth below.

Generation of Anti-CD3 Antibodies

Anti-CD3 antibodies were generated as described in WO 2017/053856, which is herein incorporated by reference. An exemplary anti-CD3 antibody was selected for the production of bispecific anti-CD3/anti-FcεR1α antibodies in accordance with the present invention. Other anti-CD3 antibodies for use in preparing bispecific antibodies in accordance with the present invention can be found in, e.g., WO 2014/047231.

Certain biological properties of the exemplary anti-CD3 antibodies generated in accordance with the methods of this Example are described in detail in the Examples herein.

Generation of Bispecific Antibodies that Bind FcεR1α and CD3

The present invention provides bispecific antigen-binding molecules that bind CD3 and FcεR1α; such bispecific antigen-binding molecules are also referred to herein as "anti-FcεR1α/anti-CD3 or anti-FcεR1α×CD3 bispecific molecules." The anti-FcεR1α portion of the anti-FcεR1α/anti-CD3 bispecific molecule is useful for targeting cells that express FcεR1α, and the anti-CD3 portion of the bispecific molecule is useful for activating T-cells. The simultaneous binding of FcεR1α on a cell and CD3 on a T-cell facilitates directed killing (cell lysis) of the targeted FcεR1α expressing cell by the activated T-cell.

Bispecific antibodies comprising an anti-FcεR1α-specific binding domain and an anti-CD3-specific binding domain were constructed using standard methodologies, wherein the anti-FcεR1α antigen binding domain and the anti-CD3 antigen binding domain each comprise different, distinct HCVRs paired with a common LCVR. In exemplified bispecific antibodies, the molecules were constructed utilizing a heavy chain from an anti-CD3 antibody, a heavy chain from an anti-FcεR1α antibody and a common light chain from the anti-CD3 antibody WO 2017/053856). In other instances, the bispecific antibodies may be constructed utilizing a heavy chain from an anti-CD3 antibody, a heavy chain from an anti-FcεR1α antibody and a light chain from an anti-CD3 antibody or a light chain from an anti-FcεR1α antibody light chain or any other light chain known to be promiscuous or pair effectively with a variety of heavy chain arms. The anti-FcεR1α antibodies and the anti-CD3 antibodies, from which any components of the bispecific antibodies are derived, are sometimes referred to as parental antibodies.

The bispecific antibodies described in the following examples comprise anti-CD3 binding arms; and anti-FcεR1α binding arm. Exemplified bispecific antibodies were manufactured having an IgG4 Fc domain (bsAb24919D, bsAb24920D, and bsAb24921 D).

A summary of the component parts of the antigen-binding domains of the various anti-FcεR1α×CD3 bispecific antibodies constructed is set forth in Table 5.

Example 2: Heavy and Light Chain Variable Region Amino Acid and Nucleic Acid Sequences Table 1 sets forth the amino acid sequence identifiers of the heavy and light chain variable regions (HCVR and LCVR), CDRs and heavy chains and light chains (HC and LC) of selected anti-FcεR1α antibodies of the invention. The corresponding nucleic acid sequence identifiers are set forth in Table 2.

TABLE 1

Amino Acid Sequence Identifiers

| Antibody Designation | SEQ ID NOs: | | | | | | | | | |
|---|---|---|---|---|---|---|---|---|---|---|
| | HCVR | HCDR1 | HCDR2 | HCDR3 | LCVR | LCDR1 | LCDR2 | LCDR3 | HC | LC |
| mAb17110 | 2 | 4 | 6 | 8 | 26 | 28 | 30 | 32 | 34 | 40 |
| mAb17111 | 10 | 12 | 14 | 16 | 26 | 28 | 30 | 32 | 36 | 40 |
| mAb17112 | 18 | 20 | 22 | 24 | 26 | 28 | 30 | 32 | 38 | 40 |

TABLE 2

Nucleic Acid Sequence Identifiers

| Antibody Designation | SEQ ID NOs: | | | | | | | | | |
|---|---|---|---|---|---|---|---|---|---|---|
| | HCVR | HCDR1 | HCDR2 | HCDR3 | LCVR | LCDR1 | LCDR2 | LCDR3 | HC | LC |
| mAb17110 | 1 | 3 | 5 | 7 | 25 | 27 | 29 | 31 | 33 | 39 |
| mAb17111 | 9 | 11 | 13 | 15 | 25 | 27 | 29 | 31 | 35 | 39 |
| mAb17112 | 17 | 19 | 21 | 23 | 25 | 27 | 29 | 31 | 37 | 39 |

Table 3 sets forth the amino acid sequence identifiers of the heavy and light chain variable regions (HCVR and LCVR), CDRs and heavy chain and light chain (HC and LC) of an exemplary anti-CD3 antibody of the invention. The corresponding nucleic acid sequence identifiers are set forth in Table 4.

TABLE 3

Amino Acid Sequence Identifiers

| Antibody Designation | SEQ ID NOs: | | | | | | | | | |
|---|---|---|---|---|---|---|---|---|---|---|
| | HCVR | HCDR1 | HCDR2 | HCDR3 | LCVR | LCDR1 | LCDR2 | LCDR3 | HC | LC |
| mAb7221G20 | 42 | 44 | 46 | 48 | 26 | 28 | 30 | 32 | 56 | 40 |

TABLE 4

Nucleic Acid Sequence Identifiers

| Antibody Designation | SEQ ID NOs: | | | | | | | | | |
|---|---|---|---|---|---|---|---|---|---|---|
| | HCVR | HCDR1 | HCDR2 | HCDR3 | LCVR | LCDR1 | LCDR2 | LCDR3 | HC | LC |
| mAb7221G20 | 41 | 43 | 45 | 47 | 25 | 27 | 29 | 31 | 55 | 39 |

A summary of the component parts of the various anti-FcεR1α×CD3 bispecific antibodies constructed is set forth in Table 5. Tables 6, 7 and 8 list the HCVR, LCVR, CDRs and heavy chain and light sequence identifiers of the bispecific antibodies.

TABLE 5

Summary of Component Parts of Anti-FcεR1α16 × CD3 Bispecific Antibodies

| Bispecific Antibody Identifier | Anti-FcεR1α Antigen-Binding Domain Heavy Chain Variable Region | Anti-CD3 Antigen-Binding Domain Heavy Chain Variable Region | Common Light Chain Variable Region |
|---|---|---|---|
| bsAb24919D | mAb17110 | mAb7221G20 | mAb7221G20 |
| bsAb24920D | mAb17111 | mAb7221G20 | mAb7221G20 |
| bsAb24921D | mAb17112 | mAb7221G20 | mAb7221G20 |

TABLE 6

Amino acid sequences of variable regions and CDRs of bispecific antibodies

| Bispecific Antibody Identifier | Anti-FcεR1α antigen-binding domain SEQ ID NOs. | | | | Anti-CD3 antigen-binding domain SEQ ID NOs. | | | | Common Light chain variable region SEQ ID NOs | | | |
|---|---|---|---|---|---|---|---|---|---|---|---|---|
| | HCVR | HCDR1 | HCDR2 | HCDR3 | HCVR | HCDR1 | HCDR2 | HCDR3 | LCVR | LCDR1 | LCDR2 | LCDR3 |
| bsAb24919D | 2 | 4 | 6 | 8 | 42 | 44 | 46 | 48 | 26 | 28 | 30 | 32 |
| bsAb24920D | 10 | 12 | 14 | 16 | 42 | 44 | 46 | 48 | 26 | 28 | 30 | 32 |
| bsAb24921D | 18 | 20 | 22 | 24 | 42 | 44 | 46 | 48 | 26 | 28 | 30 | 32 |

TABLE 7

Heavy chain and light chain amino acid sequence identifiers of bispecific antibodies

| Bispecific antibody Identifier | Anti-FcεR1α Heavy Chain | Anti-CD3 Heavy Chain | Common Light Chain |
|---|---|---|---|
| bsAb24919D | SEQ ID NO: 50 | SEQ ID NO: 56 | SEQ ID NO: 40 |
| bsAb24920D | SEQ ID NO: 52 | SEQ ID NO: 56 | SEQ ID NO: 40 |
| bsAb24921D | SEQ ID NO: 54 | SEQ ID NO: 56 | SEQ ID NO: 40 |

TABLE 8

Heavy chain and light chain nucleic acid sequence identifiers of bispecific antibodies

| Bispecific antibody Identifier | Anti-FcεR1α Heavy Chain | Anti-CD3 Heavy Chain | Common Light Chain |
|---|---|---|---|
| bsAb24919D | SEQ ID NO: 49 | SEQ ID NO: 55 | SEQ ID NO: 39 |
| bsAb24920D | SEQ ID NO: 51 | SEQ ID NO: 55 | SEQ ID NO: 39 |
| bsAb24921D | SEQ ID NO: 53 | SEQ ID NO: 55 | SEQ ID NO: 39 |

Example 3: Surface Plasmon Resonance Derived Binding Affinities and Kinetic Constants of Human Monoclonal Anti-FcεR1α Monospecific and Anti-FcεR1α16×CD3 Bispecific Antibodies Equilibrium dissociation constants ($K_D$) for human or cynomolgus FcεR1α ectodomain binding to purified anti-FcεR1α monoclonal antibodies (mAbs) and CD3×FcεR1α bispecific antibodies (bsAbs) were determined using a real-time surface plasmon resonance biosensor (SPR-Biacore), Biacore 8k. All binding studies were performed in 10 mM HEPES, 150 mM NaCl, 3 mM EDTA, and 0.05% v/v surfactant Tween-20, pH 7.4 (HBS-ET) running buffer at 25° C. and 37° C.

The Biacore CM4 sensor surface was first derivatized by amine coupling with a monoclonal mouse anti-human Fc antibody to capture approximately 500-900 RUs anti-FcεR1α monoclonal antibodies or anti-CD3×FcεR1α bispecific monoclonal antibodies. 1 RU (response unit) represents 1 pg of protein per mm², as defined by the manufacturer. The ectodomain of human and cynomolgus FcεR1α reagents were expressed with a C-term myc-myc-6×His tag-hFcεR1α.MMH (SEQ ID NO: 57) and mfFcεR1α.MMH (SEQ ID NO: 58). Different concentrations of FcεR1α reagents were prepared in HBS-ET running buffer (600 nM-7.4 nM; serially diluted by 3-fold) and injected over anti-human Fc captured anti-FcεR1α monoclonal antibodies or anti-CD3×FcεR1α bispecific monoclonal antibodies surfaces for 1 minute at a flow rate of 30 μL/minute. The dissociation of bound FcεR1α reagents was monitored for 4 minutes in HBS-ET running buffer. Association ($k_a$) and dissociation ($k_d$) rate constants were determined by fitting the real-time binding sensorgrams to a 1:1 binding model with mass transport limitation using Biacore 8k evaluation software. Binding dissociation equilibrium constants ($K_D$) and dissociative half-lives (t½) were calculated from the kinetic rate constants as:

$$K_D(M) = \frac{kd}{ka}, \text{ and } t1/2 \text{ (min)} = \frac{\ln(2)}{60*kd}$$

Binding kinetics parameters for hFcεR1α.MMH and mfFcεR1α.MMH binding to different exemplary anti-FcεR1α monoclonal antibodies or anti-CD3×FcεR1α bispecific monoclonal antibodies of the invention at 25° C. and 37° C. are shown in Table 9 through Table 12.

TABLE 9

Binding Kinetics Parameters of hFcεR1α.MMH Binding to Anti-FcεR1α Monoclonal Antibodies or Anti-CD3 × FcεR1α Bispecific Monoclonal Antibodies at 25° C.

| mAb Captured | mAb Capture Level (RU) | 600 nM hFcεR1α.MMH Bound (RU) | $k_a$ (1/Ms) | $k_d$ (1/s) | $K_D$ (M) | $t^{1/2}$ (min) |
|---|---|---|---|---|---|---|
| mAb17110 | 609 ± 1.2 | 130 | 7.19E+04 | 9.13E−03 | 1.27E−07 | 1.3 |
| mAb17111 | 567 ± 0.8 | 91 | 7.84E+04 | 1.65E−02 | 2.11E−07 | 0.7 |
| mAb17112 | 630 ± 0.9 | 123 | 8.80E+04 | 1.84E−02 | 2.09E−07 | 0.63 |
| bsAb24919D | 610 ± 0.7 | 72 | 6.82E+04 | 1.04E−02 | 1.52E−07 | 1.1 |
| bsAb24920D | 573 ± 1 | 46 | 6.59E+04 | 2.00E−02 | 3.03E−07 | 0.6 |
| bsAb24921D | 607 ± 0.6 | 69 | 7.74E+04 | 2.12E−02 | 2.74E−07 | 0.54 |
| Isotype Control mAb | 545 ± 1.7 | −5 | NB * | NB * | NB * | NB * |

NB * indicates that no binding was observed under the current experimental conditions.

TABLE 10

Binding Kinetics Parameters of hFcεR1α.MMH Binding to Anti-FcεR1α Monoclonal Antibodies or Anti-CD3 × FcεR1α Bispecific Monoclonal Antibodies at 37° C.

| mAb Captured | mAb Capture Level (RU) | 600 nM hFcεR1α.MMH Bound (RU) | $k_a$ (1/Ms) | $k_d$ (1/s) | $K_D$ (M) | $t^{1/2}$ (min) |
|---|---|---|---|---|---|---|
| mAb17110 | 745 ± 1.5 | 93 | 8.88E+04 | 3.94E−02 | 4.44E−07 | 0.29 |
| mAb17111 | 745 ± 2.2 | 52 | 8.21E+04 | 4.83E−02 | 5.88E−07 | 0.24 |
| mAb17112 | 681 ± 0.6 | 87 | 1.13E+05 | 5.85E−02 | 5.17E−07 | 0.20 |
| bsAb24919D | 764 ± 1.5 | 43 | 7.35E+04 | 5.88E−02 | 8.01E−07 | 0.20 |
| bsAb24920D | 743 ± 3.5 | 19 | 6.39E+04 | 9.91E−02 | 1.55E−06 | 0.12 |
| bsAb24921D | 670 ± 0.6 | 40 | 9.56E+04 | 9.34E−02 | 9.77E−07 | 0.12 |
| Isotype Control mAb | 688 ± 3.5 | −2 | NB * | NB * | NB * | NB * |

NB * indicates that no binding was observed under the current experimental conditions.

TABLE 11

Binding Kinetics Parameters of mFcεR1α.MMH Binding to Anti-FcεR1α Monoclonal Antibodies or Anti-CD3 × FcεR1α Bispecific Monoclonal Antibodies at 25° C.

| mAb Captured | mAb Capture Level (RU) | 600 nM mFceR1a.MMH Bound (RU) | $k_a$ (1/Ms) | $k_d$ (1/s) | $K_D$ (M) | $t^{1/2}$ (min) |
|---|---|---|---|---|---|---|
| mAb17110 | 596 ± 0.8 | 79 | 6.13E+04 | 1.36E−02 | 2.21E−07 | 0.8 |
| mAb17111 | 620 ± 0.5 | 60 | 5.55E+04 | 1.37E−02 | 2.47E−07 | 0.8 |
| mAb17112 | 594 ± 1.3 | 110 | 7.13E+04 | 1.39E−02 | 1.95E−07 | 0.8 |
| bsAb24919D | 597 ± 0.8 | 40 | 3.96E+04 | 1.44E−02 | 3.63E−07 | 0.8 |
| bsAb24920D | 625 ± 0.8 | 26 | 4.17E+04 | 1.95E−02 | 4.67E−07 | 0.6 |
| bsAb24921D | 563 ± 0.8 | 60 | 6.29E+04 | 1.61E−02 | 2.56E−07 | 0.7 |
| Isotype Control mAb | 610 ± 1.6 | −9 | NB * | NB * | NB * | NB * |

NB * indicates that no binding was observed under the current experimental conditions.

TABLE 12

Binding Kinetics Parameters of mFcεR1α.MMH Binding to
Anti-FcεR1α Monoclonal Antibodies or Anti-CD3 ×
FcεR1α Bispecific Monoclonal Antibodies at 37° C.

| mAb Captured | mAb Capture Level (RU) | 600 nM mfFcεR1a.MMH Bound (RU) | $k_a$ (1/Ms) | $k_d$ (1/s) | $K_D$ (M) | $t^{1\!/_{\!2}}$ (min) |
|---|---|---|---|---|---|---|
| mAb17110 | 719 ± 3.5 | 53 | 5.94E+04 | 2.54E−02 | 4.28E−07 | 0.45 |
| mAb17111 | 720 ± 3.4 | 38 | 5.17E+04 | 2.64E−02 | 5.10E−07 | 0.44 |
| mAb17112 | 769 ± 0.7 | 81 | 9.94E+04 | 3.28E−02 | 3.30E−07 | 0.35 |
| bsAb24919D | 685 ± 1.7 | 20 | 3.86E+04 | 3.99E−02 | 1.03E−06 | 0.29 |
| bsAb24920D | 660 ± 2.7 | 10 | 1.33E+04 | 4.45E−02 | 3.35E−06 | 0.26 |
| bsAb24921D | 749 ± 1.2 | 37 | 8.56E+04 | 4.45E−02 | 5.20E−07 | 0.26 |
| Isotype Control mAb | 775 ± 2.8 | −9 | NB * | NB * | NB * | NB * |

NB * indicates that no binding was observed under the current experimental conditions.

At 25° C., exemplary anti-FcεR1α monoclonal antibodies or anti-CD3×FcεR1α bispecific monoclonal antibodies of the invention bound to hFcεR1α.MMH with $K_D$ values ranging from 127 nM to 303 nM, as shown in Table 9. At 37° C., exemplary anti-FcεR1α monoclonal antibodies or anti-CD3×FcεR1α bispecific monoclonal antibodies of the invention bound to hFcεR1α.MMH with $K_D$ values ranging from 444 nM to 1.55 uM, as shown in Table 10.

At 25° C., exemplary anti-FcεR1α monoclonal antibodies or anti-CD3×FcεR1α bispecific monoclonal antibodies of the invention bound to mfFcεR1α.MMH with $K_D$ values ranging from 195 nM to 467 nM, as shown in Table 11. At 37° C., exemplary anti-FcεR1α monoclonal antibodies or anti-CD3×FcεR1α bispecific monoclonal antibodies of the invention bound to mfFcεR1α.MMH with $K_D$ values ranging from 330 nM to 3.35 uM, as shown in Table 12.

Example 4: Anti-FcεR1α×CD3 Bispecific Antibodies Bind Specifically to Expressed FcεR1α on Jurkat and HEK293 Cells In order to assess the binding to antigens expressed on cells by anti-FcεR1α monoclonal antibodies and anti-FcεR1α×CD3 bi-specific antibodies, flow cytometry experiment was performed with Jurkat/NFAT-Luc and HEK293/hFcεR1α/hFcεR1β/hFcεR1γ cells. Jurkat/NFAT-Luc cells are Jurkat cells engineered to stably express a luciferase reporter under the transcription control of Nuclear factor of activated T-cells (NFAT) response element. HEK293/hFcεR1α/hFcεR1β/hFcεR1γ cells are HEK293 cells engineered to stably express human FcεR1α, FcεR1β and FcεR1γ. To test the binding to monkey (cynomolgus, mf) FcεR1α (amino acids 4-260 of accession #XP_005541370.1 with alanine at position 81 changed to tryptophan), mfFcεR1α was stably expressed in HEK293 along with human FcεR1β and FcεR1γ. The resulting cell line, referred to hereafter as HEK293/mf FcεR1α/hFcεR1β/hFcεR1γ was isolated and maintained in DMEM medium supplemented with 10% FBS, 1×NEAA, 1×Penicillin/Streptomycin/L-Glutamine, 1 µg/mL Puromycin, 100 µg/mL of Hygromycin B and 500 µg/ml of G418 sulfate. The reagents information is as follows: DMEM medium, Irvine Scientific, Cat #CRL-1573; Fetal bovine serum (FBS), Seradigm, Cat #1500-500; 100× Penicillin/Streptomycin/L-Glutamine (Pen/Strep/Glut), Invitrogen, Cat #10378-016; 100×Non-essential amino acids (NEAA), Irvine Scientific, Cat #9034; Geneticin™ Selective Antibiotic (G418 Sulfate), Invitrogen, Cat #11811-098; Hygromycin B, Calbiochem, Cat #400049; Puromycin, Sigma, Cat #P-8833.

For flow cytometry analysis, HEK293, HEK293/hFcεR1α/hFcεR1β/hFcεR1γ and HEK293/mf FcεR1α/hFcεR1β/hFcεR1γ cells were collected after dissociation using Enzyme Free Dissociation Buffer (Millipore Cat #S-004), and the cells were pre-incubated with or without 70 nM human IgE, for 30 minutes on ice in FACS buffer (PBS, without $Ca^{++}$ and $Mg^{++}$, (Irvine Scientific, Cat #9240) containing 2% FBS). Jurkat/NFAT-luc cells were also collected. The antibodies at the concentration of 70 nM were then added to $1\times10^6$ cells/well of each cell type at 4° C. for 30 minutes. After incubation with primary antibodies, the cells were stained with 1.3 µg/ml of Allophycocyanin (APC) conjugated anti-human IgG secondary antibody (Jackson ImmunoResearch, Cat #109-136-170) for 30 minutes on ice. Cells were fixed using BD CytoFix™ (Becton Dickinson, Cat. #554655) and analyzed on Accuri™ C6 (BD) or Cyto-FLEX Flow cytometer (Beckman Coulter). Unstained and secondary antibody alone controls were also tested for all cell lines and a sample was evaluated for viability using the Far Red Fluo viability dye (Thermo Fisher, Cat #L10120) according to the manufacturer's protocol. The results were analyzed using FlowJo software (version 10.0.8, FlowJo) to determine the geometric means of fluorescence for viable cells and the binding ratio was calculated with the mean fluorescence intensity (MFI) of the experimental condition normalized by the MFI of the unstained respective cells. The results were summarized in Tables 13 and 14.

TABLE 13

Binding of 70 nM of Anti-FcεR1α Antibodies
and Anti-FcεR1α × CD3 Antibodies
to HEK293/hFcεR1α/hFcεR1β/hFcεR1γ and Jurkat/NFAT-luc Cells

| | | Binding Ratio (MFI of Treated/MFI of Unstained) | | | |
|---|---|---|---|---|---|
| | | HEK293 | HEK293/hFcεR1α/ hFcεR1β/hFcεR1γ | | Jurkat/ NFAT-luc |
| Antibodies ID | Specificity | No IgE | No IgE | 70 nM IgE | No IgE |
| bsAb24919D | FcεR1α × hCD3 | 2 | 269 | 277 | 48 |
| bsAb24920D | FcεR1α × hCD3 | 4 | 248 | 201 | 48 |

TABLE 13-continued

Binding of 70 nM of Anti-FcεR1α Antibodies
and Anti-FcεR1α × CD3 Antibodies
to HEK293/hFcεR1α/hFcεR1β/hFcεR1γ and Jurkat/NFAT-luc Cells

| | | Binding Ratio (MFI of Treated/MFI of Unstained) | | | |
|---|---|---|---|---|---|
| | | | HEK293/hFcεR1α/hFcεR1β/hFcεR1γ | | Jurkat/NFAT-luc |
| Antibodies ID | Specificity | HEK293 No IgE | No IgE | 70 nM IgE | No IgE |
| bsAb24921D | FcεR1α × hCD3 | 11 | 253 | 295 | 94 |
| mAb17110 | FcεR1α | 2 | 171 | 396 | 1 |
| mAb17111 | FcεR1α | 1 | 136 | 369 | 1 |
| mAb17112 | FcεR1α | 8 | 158 | 367 | 1 |
| Human IgG4 Stealth Control | Irrelevant protein | 1 | 1 | 1 | 2 |
| Human IgG4 Control | Irrelevant protein | 1 | 1 | 1 | 1 |

TABLE 14

Binding of 70 nM of Anti-FcεR1α Antibodies and Anti-FcεR1α × CD3ε Antibodies to HEK293/mf FcεR1α/hFcεR1β/hFcεR1γ Cells

| | | Binding Ratio (MFI of Treated/MFI of Unstained) | | |
|---|---|---|---|---|
| | | HEK293 Parental | HEK293/mfFcεR1α/hFcεR1β/hFcεR1γ | |
| Antibodies ID | Specificity | No IgE | No IgE | 70 nM IgE |
| bsAb24919D | FcεR1α × hCD3 | 1 | 166 | 236 |
| bsAb24920D | FcεR1α × hCD3 | 2 | 142 | 169 |
| bsAb24921D | FcεR1α × hCD3 | 2 | 169 | 284 |
| mAb17110 | FcεR1α | 1 | 101 | 256 |
| mAb17111 | FcεR1α | 1 | 102 | 190 |
| mAb17112 | FcεR1α | 1 | 134 | 279 |
| Human IgG4 Stealth Control | Irrelevant protein | 1 | 1 | 1 |
| Human IgG4 Control | Irrelevant protein | 1 | 1 | 1 |

As shown in Table 13, exemplary anti-FcεR1α×CD3 bispecific antibodies bsAb24919D, bsAb24920D, and bsAb24921D, showed binding to human FcεR1α expressed in HEK293/hFcεR1α/hFcεR1β/hFcεR1γ cells without and with 70 nM of human IgE with binding ratios of 201-295 and to and human CD3 expressed in Jurkat cells with binding ratios of 48-94. The exemplary bispecific antibodies of the invention showed minimal binding to HEK293 without FcεR1 receptors with binding ratios of 2-11. Anti-FcεR1α antibodies showed binding to HEK293/hFcεR1α/hFcεR1β/hFcεR1γ cells without and with 70 nM of human IgE with binding ratios of 136-396 and to HEK293 or Jurkat cells with binding ratios 1-8. Isotype control antibodies showed no binding to any of the cells and secondary only controls showed binding ratios of 1.

As shown in Table 14, exemplary anti-FcεR1α×CD3E bispecific antibodies bsAb24919D, bsAb24920D, and bsAb24921D, showed binding to monkey (cynomolgus) FcεR1α expressed in HEK293/mfFcεR1α/hFcεR1β/hFcεR1γ cells without and with 70 nM of human IgE of 142-284. The exemplary bi-specific antibodies of the invention showed minimal binding to HEK293 cells without FcεR1 receptors with binding ratios of 1-2. Exemplary anti-FcεR1α antibodies of the invention showed binding to HEK293/mfFcεR1α/hFcεR1β/hFcεR1γ cells without and with 70 nM of human IgE with binding ratios of 101-279 but not to HEK293. Isotype control antibodies showed no binding to any of the cells and secondary only controls showed binding ratios of 1.

Example 5: Activation of Human CD3 Signaling by Anti-FcεR1α×CD3 Bispecific Antibodies In order to assess the activation of human CD3 signaling by anti-FcεR1α×CD3ε bi-specific antibodies in the presence of FcεR1α expressing cells, a bioassay with Jurkat/NFAT-luc and HEK293/hFcεR1α/hFcεR1β/hFcεR1γ cells was performed. Stable cell lines were developed. Jurkat cell line, a human T lymphocytic cell line, has been utilized to demonstrate CD3 mediated T cell receptor signaling (Abraham and Weiss, *Jurkat T cells and development of the T-cell receptor signaling paradigm*. Nat Rev Immunol. 2004 April; 4(4):301-8). Jurkat cells were engineered to stably express a luciferase reporter under the transcription control of Nuclear factor of activated T-cells (NFAT) response element. The resulting cell line, referred to hereafter as Jurkat/NFAT-Luc was isolated and maintained in RPMI1640 medium (Irvine Scientific, Cat. #9160) supplemented with 10% FBS, 1× Penicillin/Streptomycin/L-Glutamine and 1 µg/mL Puromycin. Additionally, HEK293 cells were transfected to stably express human FcεR1α (amino acids 1-257 of Uniprot #P12319-1), FcεR1β (amino acids 1-244 of Uniprot #Q01362-1) and FcεR1γ (amino acids 1-86 of Uniprot #P30273-1). The resulting cell line, referred to hereafter as HEK293/hFcεR1α/hFcεR1β/hFcεR1γ was isolated and maintained in DMEM medium (Irvine Science, Cat. #9033) supplemented with 10% FBS, 1×NEAA, 1× Penicillin/Streptomycin/L-Glutamine, 1 µg/mL Puromycin, 100 µg/mL of Hygromycin B and 500 µg/ml of G418 sulfate.

A bioassay was performed to measure the CD3 signaling by exemplary anti-FcεR1α×CD3ε bi-specific antibodies of the invention. For the bioassay, HEK293 or HEK293/hFcεR1α/hFcεR1β/hFcεR1γ cells were plated at 10,000 cells per well in a 96-well plate in assay buffer with or without 10 nM of human IgE in assay buffer (10% FBS in RPMI1640 (Irvine Scientific, Cat #9160) with pen/strep/glut) for 30 minutes at 37° C. in 5% $CO_2$. Following the incubation, Jurkat/NFAT-luc cells were plated at 50,000 along with serially diluted exemplary anti-FcεR1α×CD3 bispecific antibodies of the invention, exemplary anti-FcεR1α of the invention or isotype control antibodies at concentrations ranging from 100 nM to 2 pM plus a sample containing buffer alone (no antibody). After 5.5 hours at 37° C. in 5% $CO_2$, luciferase activity was measured with One-Glo™ reagent (Promega, #E6031) and Victor™ X multilabel plate reader (Perkin Elmer). The results were analyzed using nonlinear regression (4-parameter logistics) with Prism™6 software (GraphPad) to obtain $EC_{50}$ values. The fold activation was calculated with the average RLU (relative light units) at the highest concentration of antibody normalized by the average RLU without antibody. The results were summarized in Table 15.

TABLE 15

Activation of Human CD3 by Anti-FcεR1α × CD3 Antibodies

| Antibody ID | Specificity | Jurkat/NFAT-luc HEK293 cells | | Jurkat/NFAT-luc HEK293/hFcεR1α/hFcεR1β/hFcεR1γ cells | | | |
|---|---|---|---|---|---|---|---|
| | | No IgE $EC_{50}$ [M] | 10 nM IgE $EC_{50}$ [M] | No IgE | | 10 nM IgE | |
| | | | | $EC_{50}$ [M] | Fold Activation | $EC_{50}$ [M] | Fold Activation |
| bsAb24919D | FcεR1α × hCD3 | No activation | No activation | 3.4E−10 | 32 | 1.5E−09 | 32 |
| bsAb24920D | FcεR1α × hCD3 | No activation | No activation | 6.8E−10 | 23 | 4.9E−09 | 25 |
| bsAb24921D | FcεR1α × hCD3 | No activation | No activation | 2.3E−10 | 24 | 1.1E−09 | 27 |
| mAb17110 | FcεR1α | No activation | No activation | No activation | 1 | No activation | 1 |
| mAb17111 | FcεR1α | No activation | No activation | No activation | 1 | No activation | 1 |
| mAb17112 | FcεR1α | No activation | No activation | No activation | 1 | No activation | 1 |
| Human IgG4 Stealth Control | Irrelevant protein | No activation | No activation | No activation | 1 | No activation | 1 |
| Human IgG4 Control | Irrelevant protein | No activation | No activation | No activation | 1 | No activation | 1 |

As shown in Table 15, exemplary anti-FcεR1α×CD3 bispecific antibodies of the invention, bsAb24919D, bsAb24920D, and bsAb24921 D, showed activation of CD3 signaling in Jurkat/NFAT-luc cells with $EC_{50}$ values ranging from 230 pM to 680 pM in the presence of HEK293/hFcεR1α/hFcεR1β/hFcεR1γ cells without human IgE and 1.1 nM to 4.9 nM with 10 nM of human IgE. The highest activation was achieved by bsAb24919D with fold activation of 32 without and with 10 nM of IgE. The exemplary bispecific antibodies of the invention showed minimal activation in the presence of HEK293 without FcεR1 receptors with fold activation ranging 1-3. Anti-FcεR1α and isotype control antibodies showed no activation with fold activation of 1 in any of the conditions tested.

Example 6: Effect of Anti-FcεR1α× Anti-CD3 Bispecific Antibodies in In Vitro Killing Assays To determine efficacy of exemplary anti-FcεR1α× anti-CD3 bispecific antibodies of the invention (bsAb24919D, bsAb24920D and bsAb24921 D) in inducing T cell-mediated killing of FcεR1α-expressing cells in vitro, two separate experiments were used. In one experiment, engineered HEK293/hFcεR1α/hFcεR1β/hFcεR1γ cells were used as targets, while in the second experiment primary human basophils within a total peripheral blood mononuclear cell (PBMC) population were used as targets. In both instances similar protocols were used to activate T cells prior to the killing assay: CD8+ T cells were first isolated from human leukopacks (NY Blood Center) using a RossetteSep™ Human CD8+ T cell enrichment cocktail kit (STEMCELL Technologies, Cat. #15063) and placed in culture with CD3/CD28-coated Dynabeads® (Invitrogen, Cat. #11132D) to induce activation of the T cells. On day 2-3 of culture, beads were removed using magnetic separation and the T cells were placed in culture. In one example (for use with HEK293/hFcεR1α/hFcεR1β/hFcεR1γ target cells), T cells were maintained in culture for 5 days, at which time IL-2 was added at 300 U/ml to promote viability and growth, and the T cells were used 2 days after IL-2 addition. In the second example (for use with PBMC target cells), cells were maintained in culture for one day after removal of the beads and then used for the killing assay. In both instances, activated T cells were labeled with Carboxyfluorescein succinimidyl ester (CFSE, Thermo Fischer Scientific, Cat. #C34554) prior to setting up the killing assay to enable exclusion of the cells during analysis of the results.

To determine efficacy of exemplary anti-FcεR1α× anti-CD3 bispecific antibodies of the invention in inducing T cell-mediated killing HEK293/hFcεR1α/hFcεR1β/hFcεR1γ target cells, a killing assay that uses detection of two mediators of the apoptotic cascade as readout (cleaved caspase 3 and cleaved PARP) was used. To set up the killing assay, the activated T cells were mixed with the target cells at a ratio of 10 target cells per T cell and then plated in a 96-well plate. Serial five-fold antibody dilutions ranging in final concentration from 100 nM to 10.24 fM were added to the wells, and the cells were incubated overnight at 37° C. to allow T cell-mediated killing to occur. Antibodies included exemplary anti-FcεR1α/CD3 bispecific antibodies of the invention and isotype control antibody. Following incubation, the cells were harvested and resuspended in pre-warmed BD cytofix (Cat. #554655) for 10 minutes at 37° C. Cells were then washed twice in MACS buffer (Miltenyi, Cat.#130-091-221) and made permeable by resuspending in ice-cold methanol and incubating at −20° C. for at least 30 minutes or overnight. Following permeabilization, MACS buffer was added to the cells for 10 minutes to allow cell rehydration, followed by 2 washes with MACS buffer. Cells were then incubated with Fc-blocking antibody (Ebioscience, Cat. #14-9161-73), followed by staining with an antibody cocktail containing Alexa-647-conjugated anti-cleaved caspase 3 (Cell Signaling Technology, Cat. #9602S) and a PE-conjugated anti-cleaved PARP antibodies (BD Biosciences, Cat. #552933). Cleavage of caspase 3 and PARP are obligatory steps in the activation of the apoptotic cascade that is initiated after delivery of cytotoxic lytic granules from the CD8+ T cells to the targets. Thus, specific detection of these cleaved proteins serves as a readout of killing. After staining the cells were washed, resuspended in MACS buffer and acquired using an LSRFortessa instrument (BD Biosciences). Killed cells were identified as CFSE-, and apoptotic cells within this population were identified as cleaved caspase 3+ and cleaved PARP+. Data analysis was performed using Graphpad Prism software. The data points obtained were transformed using an X=Log (X) equation, and the transformed data were subjected to a linear regression analysis and fitted into a sigmoidal dose response curve. $EC_{80}$ (eighty percent (80%) of maximal effective concentration, which includes the concentration of an antibody which induces a eighty percent (80%) response between the baseline and maximum after a specified exposure time) and top responses were derived from this analysis.

To determine efficacy of exemplary anti-FcεR1α× anti-CD3 bispecific antibodies of the invention in inducing T cell-mediated killing of primary basophils within a peripheral blood mononuclear cell (PBMC) population, an assay based on quantitation of these cells relative to the rest of the PBMC population was used. Fresh PBMCs were obtained from donor blood by Ficoll (GE Healthcare, Cat. #17-1440-03) purification and were mixed with activated T cells and antibody dilutions in a similar format as described above for the engineered HEK293/hFcεR1α/hFcεR1β/hFcεR1γ target cells. After overnight incubation, cells were harvested, incubated with a Live/Dead cell marker (Invitrogen Cat. #L34962), followed by incubation with an Fc-blocking antibody and staining with an antibody mix containing APC-conjugated anti-HLA-DR (BD Biosciences, Cat. #559866) and BUV 395-conjugated anti-CD123 (BD Biosciences, Cat. #564195) antibodies. The cells were then washed twice with MACS buffer and fixed in a solution containing BD Cytofix diluted 1:4 in PBS for 15 minutes. Cells were resuspended in MACS buffer and acquired in a LSRFortessa instrument. Dead cells were excluded from analysis using the Live/Dead cell marker, as were exogenous activated T cells that had previously been labeled with CFSE. Basophils within the remaining live PBMC population were identified as CD123+ HLA-DR−.

Data analysis was performed using Graphpad Prism software. The data points obtained were transformed using an X=Log(X) equation, and the transformed data were subjected to a linear regression analysis and fitted into a sigmoidal dose response curve. $EC_{50}$s were derived from this analysis. Maximum percent basophil decrease was calculated using the following formula: 100−(100× percent basophils in sample with highest antibody dose)/(Average percent basophils in all isotype control samples).

Table 16 summarizes dose-dependent increases in cleaved caspase 3 and cleaved PARP double positive HEK293/hFcεR1α/hFcεR1β/hFcεR1γ target cells in the presence of each exemplary bispecific antibodies of the invention (bsAb24919D, bsAb24920D and bsAb24921 D), with $EC_{80}$s of $3.456\times10^{-11}$ M, $1.264\times10^{-10}$ M, and $6.128\times10^{-11}$ M, respectively. Because this assay is based on capturing the early stages of apoptosis, the assay is stopped before the cells are fully killed, and the maximum percent of cells staining positive for the apoptotic markers was 56.04, 56.48 and 55.83 for cells incubated with bsAb24919D, bsAb24920D and bsAb24921 D, respectively. Notably, no increases in the percentage of target cells positive for both apoptotic markers were observed when T cells were incubated together with the target cells in the absence of antibody relative to target cells incubated alone. In other words, induction of apoptosis is not observed when T cells were incubated together with the target cells in the presence of isotype control antibody only.

TABLE 16

EC80 and Maximum Percent of Apoptotic Cells From Dose Response Killing Curves of HEK293/hFcεR1α/hFcεR1β/hFcεR1γ Target Cells after Incubation with T Cells and FcεR1α × CD3 Bispecific Antibodies

| | bsAb24919D | bsAb24920D | bsAb24921D |
|---|---|---|---|
| EC80 | 3.456e−11 | 1.264e−10 | 6.128e−11 |
| Maximum percent apoptotic cells | 56.04 | 56.48 | 55.83 |

Table 17 summarizes dose-dependent decreases in basophils within the total PBMC target population in the presence of exemplary bispecific antibodies of the invention (bsAb24919D, bsAb24920D and bsAb24921 D), with $EC_{50}$s of $3.748\times10^{-9}$ M, $2.003\times10^{-8}$ M, and $4.003\times10^{-9}$ M, respectively. Basophils were decreased by 90.57%, 80.1% and 90.92% with the highest dose of bsAb24919D, bsAb24920D and bsAb24921 D, respectively, relative to the average percent of basophils within the PBMCs in all isotype-treated samples.

TABLE 17

EC50 and Maximum Percent Basophil Decrease from Dose Response Killing Curves of Basophils within PBMC Target Cells after Incubation with T Cells and FcεR1α × CD3 Bispecific Antibodies

| | bsAb24919D | bsAb24920D | bsAb24921D |
|---|---|---|---|
| EC50 | 3.748e−9 | 2.003e−8 | 4.003e−9 |
| Maximum percent basophil decrease | 90.57% | 80.1% | 90.92% |

Example 7: In Vivo Efficacy of Anti-FcεR1α×CD3 Bispecific Antibodies

Effect of anti-FcεR1α× anti-CD3 bispecific antibodies in the passive cutaneous anaphylaxis (PCA) in vivo model and in splenic basophil depletion was studied.

To determine efficacy of anti-FcεR1α×CD3 bispecific antibodies of the invention for blocking allergen induced mast cell degranulation, the passive cutaneous anaphylaxis (PCA) in vivo model was used. The PCA model assesses type 1 hypersensitivity and measures local mast cell activation-induced vascular permeability in ear tissue (Gilfillan, A. M. & Tkaczyk, C. Integrated signaling pathways for mast-cell activation. Nat. Rev. Immunol. 6, 218-230 (2006)). This model involves intradermal injection of an allergen-specific sera from allergic patients into a local area on the skin of mice that express the human high-affinity IgE receptor, FcεR1α, followed by intravenous injection of an allergen along with a dye. The allergic reaction causes capillary dilatation and increased vascular permeability at the site of sensitization, resulting in preferential accumulation of dye at this site. The dye can be extracted from the tissue and quantitated spectrophotometrically.

For the PCA assays, groups of mice humanized for FcεR1α and CD3 (n≥5 per experiment) were first injected subcutaneously with either an isotype control antibody or one of three exemplary FcεR1α×CD3 bispecific antibodies of the invention at a dose of 25 mg/kg. Five days after antibody administration, mice were injected in the ear with serum from a cat allergic individual (IgE titer 585, diluted 1:5 in PBS). The following day the mice were administered intravenously (100 μL per mouse) a solution of 1 μg/mL Fel D1 (Indoor biotech LTN-FD1-1) dissolved in 1×PBS containing 0.5% (w/v) Evan's blue dye (Sigma Aldrich, #E2129). One hour after antigen administration, mice were sacrificed, and the ears and spleens were excised and collected.

The ears were placed in 1 mL formamide and subsequently incubated for 3 days at 50° C. to extract the Evan's blue dye. The ear tissue was then removed from the formamide, blotted to remove excess liquid and weighed. Two-hundred microliter aliquots of each formamide extract were transferred to 96 well plates in duplicate. Absorbance of the resulting supernatants was measured at 620 nm. The optical density measured was converted to Evan's blue dye concentration using a standard curve and is represented as nanogram of Evan's blue dye per milligram ear tissue. Table 18 shows mean values ±the standard deviation for each group.

To assess basophils frequency a flow cytometry-based assay was used. Single cell suspensions were prepared from the collected spleens following red blood cell lysis (Sigma, Cat #R7757). The cells were then stained with a live/dead cell marker, followed by antibody staining with the antibody mixes containing BUV 395 conjugated anti-B220 (BD, Cat #563793), FITC conjugated anti-CD4 (BD, Cat #553031), FITC conjugated anti-CD8 (BD, Cat #557667) and PECy7 conjugated CD49b (EBIOSCIENCE, Cat #25-5971-82). After staining, the cells were washed twice with MACS buffer (Miltenyi Biotech Cat #130-091-221), fixed with BD Cytofix (Cat #554655) diluted 1:4 in PBS for 15 minutes, then resuspended in MACS buffer and stored at 4 degrees. On the day of acquisition, the cells were washed twice in BD Perm/wash buffer (Cat #554723) and stained for intracellular FcεR1α with the eFluor450 conjugated anti-FcεR1α (EBIOSCIENCE, Cat #48-5899-42). The cells were then acquired in an LSRFortessa instrument and analyzed using FlowJo software. Basophils were identified as B220−CD4−CD8−CD49+FcεR1α+. Percent reduction of basophils in individual antibody-administered mice was calculated with the following formula: 100−(percent splenic basophils/mean percent splenic basophils in the isotype group), where percent splenic basophils are calculated relative to total live cells in the spleen. The results are shown in Table 19.

Evan's blue dye extravasation was observed in the ears of mice that were not administered antibody or in those administered an isotype control antibody, with a mean dye quantitation of 84.06 and 82.05 ng/mg, respectively (ng/mg refers to nanogram of Evan's blue dye per milligram of tissue). Table 18 demonstrates efficacy of the exemplary anti-FcεR1α×CD3 bispecific antibodies of the invention (bsAb24919D and bsAb24921 D) in the PCA model as indicated by a significant reduction of dye extravasation in the groups treated with these antibodies when compared to isotype control. A non-statistically significant trend towards reduced dye extravasation was observed in the group treated with bsAb24920D as compared to isotype control. As shown, bsAb24919D and bsAb24921D block mast cell degranulation in the passive cutaneous in vivo model against sensitization and subsequent challenge with Fel D1 as compared to isotype control demonstrating a significant reduction in dye extravasation of 74.64 ng/mg and 75.26 ng/mg respectively, while a more modest reduction of 48.56 ng/mg was observed with bsAb24920D. Statistical significance was determined as follows: Normality of all groups was first tested with the Shapiro-Wilk normality test. Because the data in all groups was normally distributed, a one-way ANOVA analysis was applied, with a Brown-Forsythe test to determine differences in standard deviations across the groups. Significantly different standard deviations were observed; thus, a non-parametric Kruskal-Wallis test was run instead with Dunn's multiple comparison test to determine statistical significance among the groups.

Spleens from mice that were not administered antibody were found to contain an average of 0.91% of basophils relative to total live cells, while those from mice administered isotype control antibody contained an average of 0.71% of basophils. Table 19 demonstrates efficacy of exemplary FcεR1α×CD3 bispecific antibodies of the invention (bsAb24919D, bsAb24920D and bsAb24921 D) in depleting splenic basophils in the same mice from the PCA experiment described above. As shown, mice treated with any of the three antibodies showed a reduction in splenic basophils. While this reduction was significant for all three antibodies as compared to mice that were not administered antibody, the reduction was only statistically significant for mice treated with bsAb24919D when compared to the group administered an isotype control antibody. Mice treated with bsAb24919D, bsAb24920D and bsAb24921D showed 96, 93 and 92 percent reduction in basophils relative to the isotype group, respectively. Statistical significance was determined as follows: a Shapiro-Wilk normality test was first run, and all data groups we found to be normally distributed; thus, a one-way ANOVA analysis was applied, and a Brown-Forsythe test was used to test for differences in standard deviations across the groups. Significantly different standard deviations were observed in this test, so a non-parametric Kruskal-Wallis test was run instead with Dunn's multiple comparison test to determine statistical significance among the groups.

TABLE 18

Effect of Anti-FcεR1α × CD3 Bispecific Antibodies in the Passive Cutaneous Anaphylaxis (PCA) in vivo Model

| Treatment | ng Evans Blue/ mg tissue ± SD | Mean Difference compared to Isotype control |
|---|---|---|
| bsAb24919D (n = 7) | 7.41 ± 1.1 | −74.64 (**) |
| bsAb24920D (n = 7) | 33.49 ± 16.54 | −48.56 (ns) |
| bsAb24921D (n = 7) | 6.79 ± 2.77 | −75.26(**) |

25 mg/kg total antibody concentration used for all groups administered antibody
*P ≤ .05,
***P ≤ .001,
***P ≤ .0001
n = number of mice per group

TABLE 19

Effect of Anti-FcεR1α × CD3 Bispecific Antibodies in Splenic Basophil Depletion

| Treatment | Splenic Basophils (percent of live cells) | Mean Percent Decrease Relative to Average Basophils in Isotype Control group |
|---|---|---|
| bsAb24919D (n = 7) | 0.003 ± 0.0017 | 95.89 (**) |
| bsAb24920D (n = 7) | 0.005 ± 0.0018 | 92.96 (ns) |
| bsAb24921D (n = 7) | 0.003 ± 0.0026 | 92.43 (ns) |

25 mg/kg total antibody concentration used for all groups administered antibody
*P ≤ .05,
***P ≤ .001,
***P ≤ .0001
n = number of mice per group For both PCA and basophil depletion assays, ablation of cells expressing FcεR1α was achieved using exemplary anti-FcεR1α×CD3 bispecific antibodies of the invention at lower dosage. bsAb24919D and bsAb24921D showed statistically significant inhibition of the PCA response and significant basophil loss in experiments repeated at lower doses of 1 mg/kg, 5 mg/kg, and 10 mg/kg (data not shown). Efficacy is similar at doses between 5 mg/kg and 25 mg/kg for both bsAb24919D and bsAb24921D in both PCA and basophil depletion assays (data not shown).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A bispecific antigen-binding molecule comprising a first antigen-binding domain that specifically binds human CD3, and a second antigen-binding domain that specifically binds human and/or cynomolgus FcεR1α, wherein:
  the first antigen-binding domain comprises a heavy chain complementarity determining region (HCDR)1 having the amino acid sequence of SEQ ID NO:44, an HCDR2 having the amino acid sequence of SEQ ID NO:46, an HCDR3 having the amino acid sequence of SEQ ID NO:48, a light chain complementarity determining region (LCDR)1 having the amino acid sequence of SEQ ID NO:28, an LCDR2 having the amino acid sequence of SEQ ID NO:30, and an LCDR3 having the amino acid sequence of SEQ ID NO:32; and
  the second antigen-binding domain comprises:
    (i) an HCDR1 having the amino acid sequence of SEQ ID NO:4, an HCDR2 having the amino acid sequence of SEQ ID NO:6, an HCDR3 having the amino acid sequence of SEQ ID NO:8, an LCDR1 having the amino acid sequence of SEQ ID NO:28, an LCDR2 having the amino acid sequence of SEQ ID NO:30, and an LCDR3 having the amino acid sequence of SEQ ID NO:32; or
    (ii) an HCDR1 having the amino acid sequence of SEQ ID NO:12, an HCDR2 having the amino acid sequence of SEQ ID NO:14, an HCDR3 having the amino acid sequence of SEQ ID NO:16, an LCDR1 having the amino acid sequence of SEQ ID NO:28, an LCDR2 having the amino acid sequence of SEQ ID NO:30, and an LCDR3 having the amino acid sequence of SEQ ID NO:32; or
    (iii) an HCDR1 having the amino acid sequence of SEQ ID NO:20, an HCDR2 having the amino acid sequence of SEQ ID NO:22, an HCDR3 having the amino acid sequence of SEQ ID NO:24, an LCDR1 having the amino acid sequence of SEQ ID NO:28, an LCDR2 having the amino acid sequence of SEQ ID NO:30, and an LCDR3 having the amino acid sequence of SEQ ID NO:32.

2. The bispecific antigen-binding molecule of claim 1, wherein the second antigen-binding domain comprises an HCDR1 having the amino acid sequence of SEQ ID NO:4, an HCDR2 having the amino acid sequence of SEQ ID NO:6, an HCDR3 having the amino acid sequence of SEQ ID NO:8, an LCDR1 having the amino acid sequence of SEQ ID NO:28, an LCDR2 having the amino acid sequence of SEQ ID NO:30, and an LCDR3 having the amino acid sequence of SEQ ID NO:32.

3. The bispecific antigen-binding molecule of claim 1, wherein the second antigen-binding domain comprises an HCDR1 having the amino acid sequence of SEQ ID NO:12, an HCDR2 having the amino acid sequence of SEQ ID NO:14, an HCDR3 having the amino acid sequence of SEQ ID NO:16, an LCDR1 having the amino acid sequence of SEQ ID NO:28, an LCDR2 having the amino acid sequence of SEQ ID NO:30, and an LCDR3 having the amino acid sequence of SEQ ID NO:32.

4. The bispecific antigen-binding molecule of claim 1, wherein the second antigen-binding domain comprises an HCDR1 having the amino acid sequence of SEQ ID NO:20, an HCDR2 having the amino acid sequence of SEQ ID NO:22, an HCDR3 having the amino acid sequence of SEQ ID NO:24, an LCDR1 having the amino acid sequence of SEQ ID NO:28, an LCDR2 having the amino acid sequence of SEQ ID NO:30, and an LCDR3 having the amino acid sequence of SEQ ID NO:32.

5. The bispecific antigen-binding molecule of claim 1, wherein the second antigen-binding domain comprises: (a) a heavy chain variable region (HCVR) having the amino acid sequence of SEQ ID NO: 2, SEQ ID NO: 10 or SEQ ID NO: 18; and (b) a light chain variable region (LCVR) having an amino acid sequence of SEQ ID NO: 26.

6. The bispecific antigen-binding molecule of claim 5, wherein the second antigen-binding domain comprises the HCVR/LCVR amino acid sequence pair of: SEQ ID NOs: 18/26.

7. The bispecific antigen-binding molecule of claim 1, wherein the antibody or antigen-binding fragment thereof or the bispecific antigen binding molecule binds to FcεR1α expressed on a cell surface in the presence of immunoglobulin E (IgE).

8. The bispecific antigen-binding molecule of claim 1 that is a bispecific antibody.

9. The bispecific antigen-binding molecule of claim 8, wherein the bispecific antibody comprises a human IgG heavy chain constant region.

10. The bispecific antigen-binding molecule of claim 9, wherein the human IgG heavy chain constant region is isotype IgG4.

11. The bispecific antigen-binding molecule of claim 9, wherein the human IgG heavy chain constant region is isotype IgG1.

12. The bispecific antigen-binding molecule of claim 8, wherein the bispecific antibody comprises a first heavy chain comprising an amino acid sequence of SEQ ID NO: 56, a second heavy chain comprising an amino acid sequence selected from the group consisting of SEQ ID NOs: 50, 52, and 54, and a light chain comprising an amino acid sequence of SEQ ID NO: 40.

13. A pharmaceutical composition comprising the bispecific antigen-binding molecule of claim 1 and a pharmaceutically acceptable carrier or diluent.

14. A nucleic acid molecule encoding the bispecific antigen-binding molecule of claim 1.

15. A vector comprising the nucleic acid molecule of claim 14.

16. A host cell comprising the vector of claim 15.

17. A bispecific antibody comprising a first binding arm that binds human CD3 and a second binding arm that binds human FcεR1α, wherein the first binding arm comprises a heavy chain comprising the amino acid sequence of SEQ ID NO: 56 and a light chain comprising the amino acid sequence of SEQ ID NO: 40, and wherein the second binding arm comprises a heavy chain comprising the amino acid sequence selected from the group consisting of SEQ ID NOs: 50, 52, and 54, and a light chain comprising the amino acid sequence of SEQ ID NO: 40.

* * * * *